US008795981B2

(12) United States Patent
Burke et al.

(10) Patent No.: US 8,795,981 B2
(45) Date of Patent: Aug. 5, 2014

(54) CELL DETECTION

(75) Inventors: Julian Francis Burke, Hampshire (GB); Kerensa Klottrup, Hampshire (GB); Alasdair Macmillan Robertson, Bournemouth (GB)

(73) Assignee: Molecular Devices, LLC, Sunnyvale, CA (US)

( * ) Notice: Subject to any disclaimer, the term of this patent is extended or adjusted under 35 U.S.C. 154(b) by 774 days.

(21) Appl. No.: 12/537,181

(22) Filed: Aug. 6, 2009

(65) Prior Publication Data

US 2010/0062442 A1  Mar. 11, 2010

Related U.S. Application Data

(60) Provisional application No. 61/087,560, filed on Aug. 8, 2008.

(51) Int. Cl.
| | | |
|---|---|---|
| *C12Q 1/02* | (2006.01) | |
| *C12P 21/02* | (2006.01) | |
| *G01N 33/53* | (2006.01) | |
| *C12M 1/34* | (2006.01) | |
| *G01N 33/569* | (2006.01) | |

(52) U.S. Cl.
CPC ................................. *G01N 33/56966* (2013.01)
USPC ............ 435/29; 435/7.1; 435/69.1; 435/70.1; 435/288.7

(58) Field of Classification Search
None
See application file for complete search history.

(56) References Cited

U.S. PATENT DOCUMENTS

| | | | |
|---|---|---|---|
| 4,376,110 A | 3/1983 | David | |
| 2005/0005310 A1* | 1/2005 | Chisholm et al. | 800/8 |
| 2005/0118652 A1* | 6/2005 | Lee et al. | 435/7.2 |
| 2009/0191542 A1* | 7/2009 | Hodge et al. | 435/6 |

FOREIGN PATENT DOCUMENTS

| | | |
|---|---|---|
| EP | 0239400 | 9/1987 |
| EP | 0368684 | 5/1990 |
| EP | 1293783 | 3/2003 |
| EP | 0623679 | 6/2003 |
| EP | 1502649 | 2/2005 |
| EP | 1752771 | 2/2007 |
| JP | 2001-37478 A * | 2/2001 |
| WO | WO 90/02809 | 3/1990 |
| WO | WO 90/07861 | 7/1990 |
| WO | WO 03/029461 | 4/2003 |
| WO | WO 2008/148881 | 12/2008 |

OTHER PUBLICATIONS

Yoshikawa et al. Flow cytometry: An improved method for the selection of highly productive gene-amplified CHO cells using flow cytometry. Biotechnology and Bioengineering, vol. 74, No. 5, pp. 435-442, Sep. 2001.*
Newman et al. Rapid selection of mammlian cells secreting large amounts of therapeutic proteins or peptides. Nature Methods, vol. 4, No. 3, pp. i-ii, Mar. 2007.*
Yoshikawa et al. Evaluation of stable and highly productive gene amplified CHO cell line based on the location of amplified genes. Cytotechnology, vol. 33, pp. 37-46, 2000.*
European Search Report dated Oct. 25, 2006, issued in European Patent Application No. 06254200.6, filed Aug. 9, 2006.
Alt F. W., et al., "Selective multiplication of dihydrofolate reductase genes in methotrexate-resistant variants of cultured murine cells," 1978, Journal of Biological Chemistry, 253:1357.
Altmann et al. "Insect Cells as Hosts for the Expression of Recombinant Glycoproteins,"1999, Glycoconj J, 16, 109-123.
Calloway Nathaniel T. et al., "Optimized fluorescent trimethoprim derivatives for in vivo protein labeling", 2007, ChemBioChem: A European Journal of Chemical Biology, vol. 8, No. 7, p. 767-774. XP00554094.
Cormack, B. P., et al. "FACS-optimized mutants of the green fluorescent protein (GFP)," 1996, Gene 173:33-38.
Davis, J.M., Pennington, J.E., Kubler, A.-M. and Conscience, J.F. "A simple, single-step technique for selecting and cloning hybridomas for the production of monoclonal antibodies," 1982, J. Immunol. Methods., 50: 161-171.
Goding, J.W. "Antibody production by hybridomas," 1980, J. Immunol. Methods., 39(4): 285-308.
Haas, J., et al., "Codon Usage Limitations in the Expression of HIV-1 envelope glycoprotein," 1996, Curr. Biol. 6: 315-324.
Kaufman et al., "Gene expression technology: selection and coamplification of heterologous genes in mammalian cells", 1990, Methods in Enzymology, vol. 185, p. 537-566.
Kaufman R. J., et al., "Translational efficiency of polycistronic mRNAs and their utilization to express heterologous genes in mammalian cells," 1987, EMBO J 6: 187-193.
Kohler and Milstein, "Continuous cultures of fused cells secreting antibody of predefined specificity," 1975, Nature 256:495-497.
Kost and Condreay, "Recombinant baculoviruses as expression vectors for insect and mammalian cells," 1999, Curr Opin Biotechnol, 10, 428-433.
Miller Lawrence W. et al., "In vivo protein 1021 labeling with trimethoprim conjuges: a flexible chemical tag", Nature Methods, 2005, vol. 2, No. 4, p. 255-257. XP008084941.
Miller Lawrence W. et al., "Methotrexate conjugates: a molecular in vivo protein tag", Angewandte Chemie, 2004, vol. 43, No. 13, p. 1672-1675. XP002554093.
Okayama and Berg, "Bacteriophage lambda vector for transducing a cDNA clone library into mammalian cells," 1985, Mol. Cell Biol., 5: 1136-1142.
Ormö, et al., "Crystal Structure of the *Aequorea victoria* Green Fluorescent Protein," 1996, Science, 273: 1392-1395.

(Continued)

*Primary Examiner* — Jennifer Dunston
(74) *Attorney, Agent, or Firm* — Bella Fishman

(57) ABSTRACT

In one aspect the present invention provides a method of identifying a cell or cell colony which produces a polypeptide of interest, the method comprising exposing one or more cells to a marker compound which associates with a reference polypeptide, wherein production of the polypeptide of interest by the cells is linked to production of the reference polypeptide, and detecting association of the marker compound with the one or more cells, thereby identifying a cell or cell colony which produces the polypeptide of interest.

26 Claims, 12 Drawing Sheets

(56) References Cited

OTHER PUBLICATIONS

Riechmann et al., "Reshaping human antibodies for therapy," 1988, Nature, 322: 323-327.

Sharon, J., Morrison, S.L. and Kabat, E.A.. "Detection of specific hybridoma clones by replica immunoadsorption of their secreted antibodies," 1979, Proc. Natl. Acad. Sci. (USA)., 76(3): 1420-1424.

Wigler M., et al., "Transformation of Mammalian Cells with an Amplifiable Dominant-Acting Gene," 1980, Proc. Natl. Acad. Sci. USA 77: 3567-3570.

Yang, T. T., et al. "Optimized codon usage and chromophore mutations provide enhanced sensitivity with the green fluorescent protein," 1996, Nucleic Acids Res., 24(22): 4592-4593.

* cited by examiner

A

B

C

D

A

B

C

D

A B

C D

CELL DETECTION

CROSS-REFERENCES TO RELATED APPLICATIONS

This application claims priority to U.S. Provisional Patent Application No. 61/087,560, filed Aug. 8, 2008, the contents of which are incorporated by reference in the entirety.

FIELD

The present invention relates to detecting cells which produce a polypeptide of interest, for instance during the selection of cultured cell colonies using an automated picking apparatus.

BACKGROUND OF THE INVENTION

Many molecular biology techniques depend on cloning individual cells from a mixture of cells.

For example, in the production of monoclonal antibodies, an essential step is hybridoma selection, including the separation and culture of individual hybridoma clones (fused myelomas and primary mouse cells). After cell fusion, the traditional way of selecting for monoclonality is to plate out single cells into 96-well dishes. This is repeated until clonality is assured.

Similarly, understanding gene function and identification of pharmaceutical leads requires the establishment of cell lines containing transfected genes expressed at an appropriate level. Standard techniques require the co-transfection of a gene with a dominant selectable marker followed by selection for growth for example in an antibiotic such as G418 or hygromycin. The resulting colonies are then picked by hand and further analysed for gene expression (RT-PCR) and functional expression.

Ascertaining optimal conditions for cell growth and differentiation requires broad testing of growth factors and culture conditions. The evaluation of a particular treatment requires a statistical approach on a large number of individual cells. One way to achieve this is to use numerous culture dishes, several for each treatment.

This process of cloning out may be modified and automated through the use of robots. Thus, for example, the ClonePix robot (manufactured by Genetix) implements this process by picking individual colonies directly from standard semi-solid media, the media preventing migration of the dividing cells. Thus, an imaging head captures images of colonies growing in the medium under white light, and software routines allow the separation and detection of individual colonies. A picking head then picks individual colonies into a 96-well plate.

Using a robot implemented picking method, colonies can be picked into 96-well plates at a picking speed of up to 400 clones per hour and graphic software allows the user to select colonies on the basis of size, shape, brightness and proximity. Furthermore, the software allows stratification of clones into slow, medium and fast growing cells, and clones of the same class may be grouped in the same 96-well plate. This gives rise to considerable savings in subsequent tissue culture steps as all wells can be processed at the same time.

However, the robot implemented cloning method relies on visualisation solely of colony size. Thus, the image capture only provides information on the size of the colony, and all colonies within a certain size range are picked. It is known for example that different hybridoma clones are capable of producing varying amounts of antibody. No information is provided or processed as to the productivity of different cells (i.e., the quantity of product produced or secreted), and the robot implemented cloning method therefore cannot discriminate between a high-producing hybridoma cell or colony and a low-producing hybridoma cell or colony. With regard to transfected cells, the robot cannot distinguish between clones with different levels of expression and/or secretion of recombinant protein.

A method disclosed in EP1752771 addresses this issue by identifying cells producing a polypeptide of interest using a combination of a class marker and a specificity marker. Marker-polypeptide complexes can then be detected, for example by an automated imaging system, and cells producing a high level of the polypeptide picked directly by a robot. However, this method necessitates the use of specific reagents such as antibodies to characterise production of the polypeptide of interest. This requires that such specific reagents are available and that different reagents must be used for detecting different polypeptides.

As mentioned above, selectable markers are often used in the identification of cell colonies expressing a protein of interest. It is also necessary to identify cell clones in which the vector sequences are retained during cell proliferation. In some cases stable vector maintenance is achieved either by use of a viral replicon or as a consequence of integration of the vector into the host cell's DNA.

It is often preferable to use amplifiable selectable markers when a high level of expression of a gene product is desired. The copy number of the vector DNA, and consequently the amount of product which is expressed, can be increased by selecting for cell lines in which the vector sequences have been amplified (e.g. after integration into the host cell's DNA).

A known method for carrying out such a selection procedure is to transfect a host cell with a vector comprising a DNA sequence which encodes an enzyme which is inhibited by a known drug. The vector may also comprise a DNA sequence which encodes a desired protein. Alternatively the host cell may be co-transfected with a second vector which comprises the DNA sequence which encodes the desired protein.

The transfected host cells are then cultured in increasing concentrations of the known drug thereby selecting drug-resistant cells. A common mechanism leading to the appearance of mutant cells which can survive in the increased concentrations of the otherwise toxic drug is the over-production of the enzyme which is inhibited by the drug. This most commonly results from amplification of vector DNA and hence gene copy number of the enzyme.

Where drug resistance is caused by an increase in copy number of the vector DNA encoding the enzyme, there is also an increase in the copy number of the vector DNA encoding the desired protein. There is thus an increased level of production of the desired protein.

The most commonly used system for such co-amplification uses dihydrofolate reductase (DHFR) as the enzyme. DHFR can be inhibited by the drug methotrexate (MTX). To achieve co-amplification, a host cell (which may lack an active gene which encodes DHFR) is transfected with a vector which comprises DNA sequences encoding DHFR and a desired protein. The genes for DHFR and desired protein may also be co-transfected into the cell on different vectors. The transfected host cells are cultured in media containing increasing levels of MTX, and those cell lines which survive are selected.

However, a disadvantage of such existing methods is that where an amplifiable selectable marker is used, the cells need to be grown for a time corresponding to a number of cell generations in order to adequately distinguish between transfected and non-transfected cells, or rather between cells having a high or a low selectable marker (e.g. DHFR) gene copy number. This is due to the time taken for untransfected cells to die and for cells showing amplification of the marker gene to outgrow those having a lower gene copy number. This produces a significant delay to the overall selection process. Typically, the selection process may take 6 months or more using such methods.

Therefore there is still a need for an improved method for detecting a cell producing a polypeptide of interest, which avoids the need for a lengthy growth phase during dominant marker selection and which provides a simple, rapid and widely-applicable selection procedure using readily-available reagents.

BRIEF SUMMARY OF THE INVENTION

Accordingly, in one aspect the present invention provides a method of identifying a cell which produces a polypeptide of interest, the method comprising exposing one or more cells to a marker compound which associates with a reference polypeptide, wherein production of the polypeptide of interest by the cells is linked to production of the reference polypeptide, and detecting association of the marker compound with the one or more cells, thereby identifying a cell which produces the polypeptide of interest.

As used herein, in various embodiments "cell" may refer to a single cell, at least one cell, a plurality of cells or a cell colony.

In one embodiment, association of the marker compound with the one or more cells may be detected by optical imaging. For instance, the detecting step may comprise obtaining an image of the cells and analysing the image to identify association of the marker compound with a cell, thereby detecting a cell which produces the polypeptide of interest.

In one embodiment, the marker compound binds to the reference polypeptide. Detecting association of the marker compound with the cells may comprise, for example, detecting binding of the marker compound to the cells.

In one embodiment, the reference polypeptide is encoded by an amplifiable gene. For example, in one embodiment the gene encoding the reference polypeptide is amplified in the cell which is identified, e.g. a cell to which the marker compound binds. By "amplified" it is meant that there is an increase in copy number of the gene in the cell. Preferably, the gene encoding the reference polypeptide can be amplified in the cells in the presence of the marker compound. Thus the reference polypeptide may comprise a selectable marker, preferably a dominant selectable marker, more preferably an amplifiable dominant selectable marker. In further preferred embodiments, a gene encoding the polypeptide of interest is also amplified in the identified cell.

In one embodiment, the reference polypeptide comprises an enzyme, for example dihydrofolate reductase, adenosine deaminase, glutamine synthase, thymidine kinase, aminoglycoside phosphotransferase, hygromycin B phosphotransferase, xanthine-guanine phosphoribosyl transferase or asparagine synthetase.

In one embodiment, the reference polypeptide comprises an enzyme and the marker compound comprises an inhibitor of the enzyme. In an embodiment where the enzyme comprises dihydrofolate reductase, the marker compound may comprise methotrexate, trimethoprim, pyrimethamine or pemetrexed, preferably methotrexate. Where the enzyme comprises adenosine deaminase, the marker compound may comprise deoxycoformycin.

In one embodiment, the polypeptide of interest comprises a biotherapeutic molecule. For example, the polypeptide of interest may comprise an immunoglobulin or fragment thereof. In another embodiment, the polypeptide of interest comprises a receptor.

In one embodiment, the polypeptide of interest comprises a recombinant polypeptide. For instance, the polypeptide of interest may be expressed by a transfected or transformed cell, e.g. a gene encoding the polypeptide of interest may be introduced into the cells via an exogenous expression vector. Similarly the reference polypeptide may be a recombinant polypeptide, e.g. a gene encoding the reference polypeptide may be introduced into the cell on the same or a different vector to that encoding the polypeptide of interest.

Preferably the cell is a eukaryotic cell, more preferably a mammalian cell, including a human or a non-human cell, e.g. a Chinese hamster ovary (CHO) cell line such as DG44. In one embodiment, the cells are cultured cells, e.g. the method is performed in vitro on cells under cell or tissue culture conditions, wherein the cells are isolated from their natural in vivo environment.

In one embodiment, an image showing association of the marker compound with the cells is obtained and analysed. The image may be obtained, for example, by a manually operated or an automated imaging system. The (automated or manual) imaging system may, for example, automatically detect a reporter molecule such as a fluorescent label attached to the marker compound. Thus the (automated or manual) imaging system may, in one embodiment, comprise a fluorescent microscope or other imaging device capable of capturing fluorescent images. The image may be analysed to determine a level of the marker compound associated with the cell, the level being indicative of an amount of the polypeptide of interest produced by the cell. In a preferred embodiment, an automated imaging system is used to capture and automatically process the image to detect cells which produce the polypeptide of interest at a high level. Preferably, the automated imaging system is part of a robotic apparatus which is also capable of automatically picking a cell a cell or colony which is selected.

In one embodiment, the method further comprises a step of exposing the cells to an agent which binds to the polypeptide of interest and detecting binding of the agent to one or more cells. This step may, for example, be performed after a cell or cell colony has been identified as expressing the reference polypeptide.

In one embodiment the method further comprises a step of taking a diseased tissue sample on a surface and exposing the cells to an agent which binds to the polypeptide of interest and detecting binding of the agent to one or more cells. This step may, for example, be performed as a method of identifying and diagnosing disease caused by or associated with gene amplification or protein over expression in the diseased cells.

In one embodiment, the cells are pre-incubated with the marker compound. This step may be performed, for example, before the cells are exposed to a labelled marker compound and binding to the reference polypeptide is detected. In some embodiments, pre-incubating with the marker compound may cause amplification of genes encoding the reference and/or polypeptides of interest, and/or enrich or partially select for cells in which these genes are amplified.

The method may be performed on adherent or non-adherent cells, e.g. cells in suspension culture. In one embodiment, the cells are disposed on or in solid or semi-solid media, for example methylcellulose media.

In one embodiment, the polypeptide of interest is secreted by the cell. In another embodiment, the reference polypeptide is an intracellular or cell surface-associated polypeptide.

In one embodiment, the marker compound comprises a reporter molecule or label, for example fluorescent label such as a fluorophore or fluorochrome such as fluorescein, tetramethylrhodamine or phycoerythrin.

In a further aspect, the present invention provides a method of selecting a cell which produces a polypeptide of interest from a plurality of cells, comprising detecting a cell which produces the polypeptide of interest by a method as defined above, and selecting the cell by picking the detected cell.

In one embodiment the cell selection method may comprise determining a level of the marker compound associated with each cell, comparing the level to a predetermined threshold and selecting a cell having a level of the marker compound above the predetermined threshold. For example a cell which is associated with an elevated level of the marker compound may be selected, thereby selecting a cell showing an elevated amount of production of the polypeptide of interest. In one embodiment the level of the marker compound in the selected cell is elevated relative to a mean level of the marker compound in the plurality of cells.

In one embodiment, the cell is picked by an automated cell picking device.

In a further aspect, the present invention provides a method of identifying a cell which produces an amplifiable marker polypeptide, the method comprising exposing one or more cells to a marker compound which associates with the amplifiable marker polypeptide, the amplifiable marker polypeptide comprising a product of a gene which can be amplified in the cells in the presence of the marker compound, and detecting association of the marker compound with the cells, thereby identifying a cell which produces the amplifiable marker polypeptide.

According to this aspect, the amplifiable marker polypeptide corresponds to the reference polypeptide referred to above. Thus in this aspect, specific embodiments are also provided corresponding to those described above in relation to alternative aspects, for example wherein the marker compound, cell type, detection method or amplifiable marker polypeptide (reference polypeptide) is defined more precisely. Thus in one embodiment, the amplifiable marker gene is amplified in the cell which is identified.

In a further aspect, the present invention provides an automated imaging apparatus for detecting a cell or cell colony which produces a polypeptide of interest, wherein the apparatus is configured to obtain an image of one or more cells, wherein the cells have been exposed to a marker compound which associates with a reference polypeptide, production of a polypeptide of interest by the cells being linked to production of the reference polypeptide, and detect association of the marker compound with the one or more cells, by analysing the image to identify association of the marker compound with a cell, thereby detecting a cell or cell colony which produces the polypeptide of interest.

In a further aspect, the present invention provides an automated imaging apparatus for identifying a cell or cell colony which produces an amplifiable marker polypeptide, wherein the apparatus is configured to obtain an image of one or more cells, wherein the cells have been exposed to a marker compound which associates with an amplifiable marker polypeptide, the amplifiable marker polypeptide comprising a product of a gene which can be amplified in the cells in the presence of the marker compound, and detect association of the marker compound with the one or more cells, by analysing the image to identify association of the marker compound with a cell, thereby detecting a cell or cell colony which produces the amplifiable marker polypeptide.

In one embodiment, the automated imaging apparatus comprises a fluorescent imaging device such as a fluorescent microscope. The automated imaging apparatus may further comprise, for example an image acquisition device such as a camera, e.g. a CCD device. The apparatus may further comprise a processor, for example for processing the acquired image to identify cells which are associated with marker compound, e.g. cells which show high levels of fluorescence in the image.

In a further aspect the present invention provides an automated cell picking device which is configured to perform the present methods. In one embodiment, the automated cell picking device comprises an automated imaging apparatus as described above, and a cell picking head. The cell picking device may be configured to pick a cell or cell colony identified by the imaging apparatus, e.g. a cell or colony which has been identified as producing the polypeptide of interest or amplifiable marker polypeptide.

Embodiments of the present invention provide a method by which cells expressing a polypeptide of interest at a high level can be identified rapidly and efficiently, without the need for antibodies specific to the polypeptide of interest itself. The method involves using a marker compound to detect cells which express a further polypeptide. The further polypeptide may also be termed herein a reference or marker polypeptide, since expression of the reference polypeptide is linked to expression of the polypeptide of interest. This means that cells which express the reference polypeptide at high levels also produce the polypeptide of interest at high levels.

However, in contrast to known methods using amplified dominant selectable markers, which rely on growth and survival of cells having an increased gene copy number, the present invention allows the identification of highly productive cells or colonies at an earlier stage by use of a marker compound which associates with the reference polypeptide. By binding to or otherwise associating with the reference polypeptide, the marker compound can be used to label cells which produce the polypeptide of interest even before they could be fully differentiated based on their growth potential in the presence of, for example, a cytotoxic agent.

DETAILED DESCRIPTION OF THE INVENTION

Figure 1:
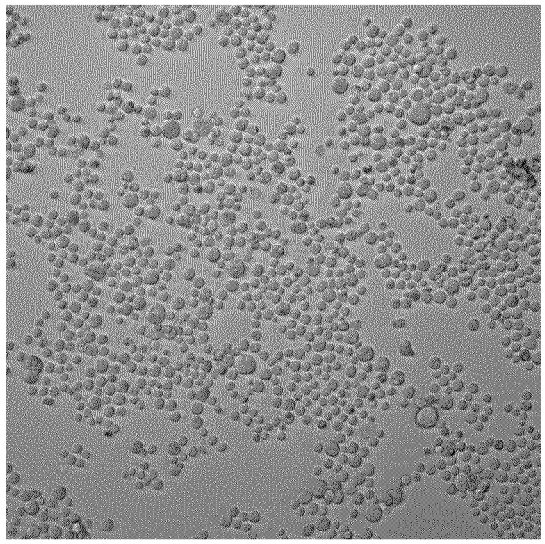
FIG. 1 shows brightfield images (panels A and C) and fluorescent images (panels B and D) of DHFR-amplified CHO DG44 cells which have been incubated in the absence (panels A and B) or presence (150 nM; panels C and D) of fluorescein-conjugated methotrexate.
Figure 1:
Figure 1:
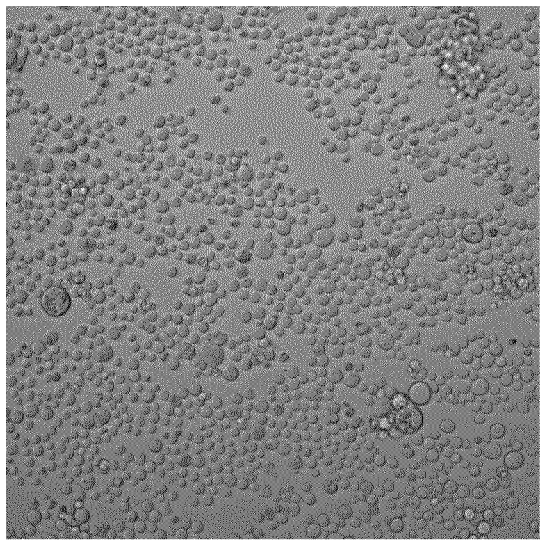
Figure 1:

The present invention provides a method of detecting a cell or colony which produces a polypeptide of interest. A marker compound is used to identify cells which produce a reference polypeptide, the expression of which is associated with expression of the polypeptide of interest. Colonies or cells of interest may then be selected and picked for further study.

The marker compound may be labelled with a reporter which is capable of emitting a signal in order to ease detection. Colonies or cells which emit signal may be chosen and picked for further manipulation.

In preferred embodiments, any of the steps set out in relation to the detection method, such as exposing the cells to a marker compound, detection of binding, as well as associated steps such as selection and/or picking of cells or colonies of interest may be conducted using automated robotic apparatus. In preferred embodiments, the robotic apparatus comprises a ClonePix FL apparatus (Genetix, New Milton, United Kingdom).

In preferred embodiments, the cells are grown on the surface of or within solid or semi-solid media. Thus, preferably, the cell or colony may be grown on agar, agarose, or methylcellulose media. In preferred embodiments, the cells or colonies are grown on a Petri dish or other similar container, although it will be appreciated that other containers may also be used, such as well plates, particularly 1 well plates, 4 well plates, 6 well plates, microtitre dishes, etc.

The cell or colony of cells may comprise any cultured cell or cell line, as known in the art. Included are prokaryotic cells and eukaryotic cells, including bacteria, yeast, insect and mammalian cells. A list of known cell lines is set out in the Cell Line Data Base (Istituto Nazionale per la Ricerca sul Cancro, Genova, Italy) and the ECACC European Collection of Cell Cultures. Specific examples of cells include *E. coli* cells, CHO cells, HeLa cells, African green monkey cells, Sf9 cells, etc. Such cells may be transfected with suitable expression vectors to enable expression of polypeptides, as described in further detail below. Other cells particularly suitable for use in the methods described here are fused cell lines, including hybridoma cell lines.

In general, when referring to "a cell" herein, unless otherwise stated it is intended to include more than one cell, a plurality of cells, or any collection of cells, e.g. a cell colony. Thus "a method of identifying a cell" includes a method of identifying two or more cells or a colony of cells (e.g. which produce a polypeptide of interest). The method can therefore be applied to picking cell colonies as well as to identifying individual cells which express a polypeptide of interest.

Specifically, the method described herein enables colonies or cells of interest, e.g., which produce polypeptides of interest to be identified. Advantageously, the colonies are visualised and imaged, and identified by software according to whether or not they emit a signal. Other characteristics, such as size, may also be used for identifying relevant colonies or cells. Selected colonies or cells may then be picked and replated, for example into 96 well plates, for growing on, using for example a ClonePix FL robotic apparatus (Genetix, New Milton, United Kingdom).

The marker compound may be chosen based on the knowledge of the nature or characteristics of reference polypeptide, as described in further detail below.

The invention enables the selection of a cell or colony which produces a polypeptide of interest by identifying cells which produce a reference polypeptide. A cell or colony may also be chosen on the basis of its productivity, i.e., how much reference polypeptide (and consequently how much polypeptide of interest) it produces. Thus, the methods described here enable the selection of high producing colonies.

The method may be applied to a number of cells or colonies, preferably a plurality of cells or colonies, simultaneously, and is capable of detecting only those cells or colonies which produce the particular product of interest.

Polypeptide of Interest

The polypeptide of interest may be, for example, an intracellular polypeptide, a membrane polypeptide or a secreted polypeptide. In one embodiment, the reference polypeptide is a secreted polypeptide, e.g. a secreted antibody such as IgG. The secreted polypeptide may form a halo or aura around the cell or colony which produces it.

In some embodiments, the method of the invention may comprise a further step of exposing the cells to an agent which associates with the polypeptide of interest. In many embodiments, this step is not necessary because association of the marker compound with the reference polypeptide provides an indication of cells which express the polypeptide of interest. However, in some cases it may be desirable to confirm that the polypeptide of interest is also expressed by the selected cells. The agent which associates with the polypeptide of interest may be, for example, a ligand or antibody which selectively binds to the polypeptide of interest. The agent which associates with the polypeptide of interest may therefore be a compound of a similar type to the marker compound (which associates with the reference polypeptide), the difference being that the agent and marker compound bind to different entities.

Preferably the polypeptide of interest is a biotherapeutic molecule, for instance a therapeutic antibody, growth factor, cytokine or other recombinant polypeptide expressed by the cell. In one embodiment, the polypeptide of interest is a recombinant polypeptide expressed by a host cell, i.e. the cell has been engineered to express the polypeptide of interest.

Exemplary polypeptides of interest include antibodies, peptibodies, immunoglobulin-like proteins, non-antibody proteins and non-immunoglobulin-like proteins, particularly biotherapeutic molecules in these classes. Such polypeptides include those with modified glycosylation, polypeptides without glycosylation (unglycosylated). As used herein, "analogs" refers to an amino acid sequence that has insertions, deletions or substitutions relative to the parent sequence, while still substantially maintaining the biological activity of the parent sequence, as determined using biological assays known to one of skill in the art. Polypeptides of interest also include derivatives of naturally occurring or analog polypeptides which have been chemically modified, for example, to attach water soluble polymers (e.g., pegylated), radionuclides, or other diagnostic or targeting or therapeutic moieties.

Exemplary polypeptides of interest include human erythropoietin, darbepoetin, granulocyte-colony stimulating factor (GCSF), stem cell factor, leptin, hormones, cytokines, hematopoietic factors, growth factors, antiobesity factors, trophic factors, anti-inflammatory factors, receptors or soluble receptors, enzymes, variants, derivatives, or analogs of any of these proteins. Other examples include insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), interleukins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase, or kallikrein, receptors or soluble receptors, enzymes, variants, derivatives, or analogs of any of these proteins.

In one embodiment, the polypeptide of interest comprises an antibody or immunoglobulin. Thus one aspect of the invention provides a method of detecting a polypeptide of interest comprising an antibody or immunoglobulin produced by a cell or cell colony. The cell or cell colony may therefore comprise an antibody producing cell, preferably an antibody secreting cell, such as a B-cell, transfected myeloma or a hybridoma.

As used herein, the term "antibody" includes fully assembled antibodies, monoclonal antibodies (including human, humanized or chimeric antibodies), multispecific antibodies (e.g., bispecific antibodies), Maxibody, and antibody fragments that can bind antigen (e.g., Fab', F'(ab)$_2$, Fv, single chain antibodies, diabodies), comprising complementarity determining regions (CDRs) of the foregoing as long as they exhibit the desired biological activity.

Exemplary antibodies are Herceptin® (Trastuzumab), a recombinant DNA-derived humanized monoclonal antibody that selectively binds to the extracellular domain of the human epidermal growth factor receptor 2 (Her2) proto-oncogene; Rituxan® (Rituximab), a genetically engineered chimeric murine/human monoclonal antibody directed against the CD20 antigen found on the surface of normal and malignant B lymphocytes; Avastin® (bevacizumab), Bexxar® (Tositumomab), Campath® (Alemtuzumab), Erbitux® (Cetuximab), Humira® (Adalimumab), Raptiva® (efalizumab), Remicade® (Infliximab), ReoPro® (Abciximab), Simulect® (Basiliximab), Synagis® (Palivizumab), Xolair® (Omalizumab), Zenapax® (Daclizumab), Zevalin® (Ibritumomab Tiuxetan), or Mylotarg® (gemtuzumab ozogamicin), receptors or soluble receptors, enzymes, variants, derivatives, or analogs of any of these antibodies.

In one embodiment, the polypeptide of interest comprises a receptor polypeptide. A receptor, as the term is used in this document, means any polypeptide which is capable of binding another molecule, preferably a small molecule such as a ligand. Preferably, a receptor is a protein molecule that receives and responds to a specific neurotransmitter, hormone, ligand or other substance. Preferably, the receptor is capable of binding an affinity ligand of the receptor.

Where the polypeptide comprises a receptor, the cell or cell colony may be a cultured cell which has been engineered to express the receptor, preferably as a recombinant protein. The cell which is transfected may be any suitable cell as known in the art, for example, suspension adapted adherent cells such as CHO-S are suitable.

The cell may be transfected with an expression vector encoding a receptor polypeptide. The receptor preferably comprises a trans-membrane receptor, and may be a peripheral membrane receptor, a transmembrane protein receptor or an intracellular receptor, such as a nuclear receptor.

The receptor may comprise a G protein-coupled receptor (GPCR), also known as a seven transmembrane receptor or 7™ receptor. For example, the receptor may comprise any of the following (ligands in brackets following): a "muscarinic" acetylcholine receptor (acetylcholine and muscarine), an adenosine receptor (adenosine), an adrenoceptor or adrenergic receptor (ligand: adrenaline, and other structurally related hormones and drugs), a GABA receptor, type-b (γ-aminobutyric acid or GABA), an angiotensin receptor (angiotensin), a cannabinoid receptor (cannabinoids), a cholecystokinin receptor (cholecystokinin), a dopamine receptor (dopamine), a glucagon receptor (glucagon), a histamine receptor (histamine), a olfactory receptor, a opioid receptor (opioids), a rhodopsin (a photoreceptor), a secretin receptor (secretin), a serotonin receptors (Serotonin, also known as 5-Hydroxytryptamine or 5-HT) or a somatostatin receptor (Somatostatin).

The receptor may comprise a tyrosine kinase receptor, such as an erythropoietin receptor (Erythropoietin), an insulin receptor (Insulin), a growth factor receptor or a cytokine receptor. The receptor may comprise a guanylyl cyclase receptor such as GC-A & GC-B, comprising receptors for Atrial-natriuretic peptide (ANP) and other natriuretic peptides or GC-C, a guanylin receptor.

The receptor may comprise an ionotropic receptor, for example a nicotinic acetylcholine receptor (Acetylcholine, Nicotine), a glycine receptor (GlyR) (Glycine, Strychnine), a GABA receptor: GABA-A, GABA-C (GABA), a glutamate receptor, an NMDA receptor, an AMPA receptor, a kainate receptor (Glutamate) or a 5-HT3 receptor (Serotonin).

Reference Polypeptide and Marker Compound

According to embodiments of the present invention, expression of the reference polypeptide is used to detect cells which produce the polypeptide of interest. Therefore the reference polypeptide may be any polypeptide whose expression is linked to production of the polypeptide of interest. By this it is meant that there is an association between levels of the reference polypeptide and polypeptide of interest in the cells such that, for example, when levels of the polypeptide of interest are elevated, levels of the reference polypeptide are also elevated and vice versa. Preferably the reference polypeptide is a recombinant polypeptide, e.g. a gene encoding the reference polypeptide has been introduced into the cell. The gene encoding the reference polypeptide may be introduced into the cell on the same vector as the polypeptide of interest, or alternatively the two polypeptides may be present on separate vectors.

For instance, the reference polypeptide may be a polypeptide whose expression is under the control of the same regulatory elements as the polypeptide of interest. In a preferred embodiment, a gene encoding the reference polypeptide is capable of being amplified within the cells together with a gene encoding the polypeptide of interest. In this embodiment, gene amplification may take place in the presence of the marker compound.

It is important that the reference polypeptide is selected such that it can be detected specifically by means of the marker compound. Suitable reference polypeptides include polypeptides which are produced by recombinant expression of exogenous selectable marker genes. Selectable markers can be detected, for example, by marker compounds which bind specifically to them, including compounds which may be used as selection compounds for growth-based identification of transfected cells in culture. However any polypeptide can be used as a reference polypeptide provided that its production can be detected either directly or indirectly and linked to expression of the polypeptide of interest.

By "a marker compound which associates with a reference polypeptide" it is meant that levels of the marker compound can be correlated with levels of the reference polypeptide. For instance, the marker compound may bind (directly) to the reference polypeptide such that binding of high levels of the marker compound to a cell is indicative of high expression of the polypeptide of interest, i.e. there is a positive correlation between the marker compound and reference polypeptide. However, in other embodiments there may be a negative correlation between the marker compound and reference polypeptide, such that low levels of the marker compound are indicative of high expression of the polypeptide of interest. In further embodiments, the marker compound may bind to a further compound, the level of which is indicative of the level of the polypeptide of interest, i.e. there is an indirect association between the marker compound and the polypeptide of interest.

In one embodiment, the reference polypeptide is an enzyme and the marker compound is an inhibitor which binds (e.g. selectively or specifically) to the enzyme. The inhibitor may be a reversible or non-reversible inhibitor and bind to the active site of the enzyme or to an allosteric site.

In another embodiment, the reference polypeptide is a receptor (e.g. a transmembrane protein present on the cell surface) and the marker compound is a ligand (including agonists and antagonists) which binds to the receptor.

In a further embodiment, the marker compound is an antibody or fragment thereof which binds to the reference polypeptide.

The reference polypeptide may be an intracellular, cell surface (e.g. membrane-associated) or secreted polypeptide. Preferably the reference polypeptide is intracellular or membrane-bound, or retained within a cell wall or a periplasmic space. In these embodiments, identification of cells expressing the reference polypeptide may be facilitated since the marker compound may bind directly to the producing cells. This may be particularly advantageous where the polypeptide of interest is secreted by the cells, since if an agent which bound directly to the polypeptide of interest were used it would not directly label expressing cells.

However, in alternative embodiments the reference polypeptide may be a secreted polypeptide, e.g. a secreted antibody such as IgG, since the secreted polypeptide may form a halo or aura around the cell or colony which produces it. Thus "detecting association of the marker compound with one or more cells" includes detecting binding of the marker compound to secreted polypeptide surrounding the cells, as well as direct binding of the marker compound to the cells themselves.

Amplifiable Markers

The ability of cloned genes to function when introduced into host cell cultures has proved to be invaluable in studies of gene expression. It has also provided a means of obtaining large quantities of proteins which are otherwise scarce or which are completely novel products of gene manipulation. It is advantageous to obtain such proteins from mammalian cells since such proteins are generally correctly folded, appropriately modified and completely functional, often in marked contrast to those proteins as expressed in bacterial cells.

A method of amplifying the gene of interest is also desirable for expression of the recombinant protein, and typically involves the use of a selection marker (reviewed in Kaufman, R. J., Meth. Enzymology 185:537 (1988)). Resistance to cytotoxic drugs is the characteristic most frequently used as a selection marker, and can be the result of either a dominant trait (i.e., can be used independent of host cell type) or a recessive trait (i.e., useful in particular host cell types that are deficient in whatever activity is being selected for).

A particularly useful selection and amplification scheme utilizes DHFR-MTX resistance. MTX is an inhibitor of DHFR that is thought to cause amplification of endogenous DHFR genes (Alt F. W., et al., *Journal of Biological Chemistry*, 253:1357, 1978) and transfected DHFR sequences (Wigler M., et al., *Proc. Natl. Acad. Sci. USA*, 77:3567, 1980). However, MTX may simply reveal cells in which amplification of DHFR has taken place, since these are the only cells which survive and continue to grow in the presence of MTX. Cells are transformed with DNA containing the gene of interest in one expression cassette, and the DHFR gene in a second expression cassette. The two genes can be in one bicistronic expression unit (Kaufman et al., 1991 supra and Kaufman R. J., et al., *EMBO J*, 6:187, 1987) in the same vector, or may be present on separate vectors. If cells are co-transfected with one vector encoding DHFR and a second encoding the protein of interest, selection of cells containing one or both vectors may be performed using media lacking hypoxanthine and thymidine to select for DHFR, and an antibiotic such as G418 to select for the vector containing the protein of interest (e.g. where the latter vector also encodes an antibiotic resistance gene). Transformed cells are grown in media containing successively greater amounts of MTX, resulting in greater expression of the DHFR gene, as well as the gene of interest. This method does not give information about the copy number of either gene but confirms their presence and stable integration.

In one embodiment, the present invention may employ a selection and amplification scheme based on the use of an amplifiable marker and a cytotoxic drug, such as the DHFR-MTX system discussed above. However, in contrast to the known methods, according to embodiments of the present invention cells expressing the polypeptide of interest are identified by, for example, detecting binding of the cytotoxic drug to the amplifiable marker, rather than by growth of cells in which the marker is amplified per se.

Various amplifiable markers are suitable for use as the reference polypeptide in the present invention. Amplifiable markers are described in general in Maniatis, *Molecular Biology: A Laboratory Manual*, Cold Spring Harbor Laboratory, N.Y., 1989; pgs 16.9-16.14. Useful selectable markers for gene amplification in drug-resistant mammalian cells are also shown in Table 1 of Kaufman, R. J., *Meth. Enzymology*. 185:537 (1988).

In particular embodiments, the reference polypeptide (dominant amplifiable selection marker) is DHFR or adenosine deaminase. In the case of DHFR as reference polypeptide the marker compound is preferably methotrexate (MTX, (S)-2-(4-(((2,4-diaminopteridin-6-yl)methyl)(methyl)amino) benzamido)pentanedioic acid, also known as amethopterin). Alternative marker compounds for DHFR include any compound or inhibitor which selectively binds to DHFR, including trimethoprim (5-(3,4,5-trimethoxybenzyl)pyrimidine-2, 4-diamine), pyrimethamine (5-(4-chlorophenyl)-6-ethyl-2,4-pyrimidinediamine) or pemetrexed (2-[4-[2-(4-amino-2-oxo-3,5,7-triazabicyclo[4.3.0]nona-3,8,10-trien-9-yl)ethyl]benzoyl]aminopentanedioic acid).

When adenosine deaminase is the reference polypeptide, an inhibitor such as 2'-deoxycoformycin (8-[4-hydroxy-5-(hydroxymethyl)tetrahydrofuran-2-yl]-4,6,8,10-tetrazabicyclo[5.3.0]deca-4,9,11-trien-2-ol, also known as pentostatin) may be used.

Incubating cells with MTX interferes with normal folic acid metabolism. Folic acid, the core structure of all folates, is not useful until it is chemically reduced. The enzyme that reduces folic acid is dihydrofolate reductase (DHFR). DHFR reduces dihydrofolate into tetrahydrofolate (active folate). It is this compound that is used as a donor of methyl groups. The methyl groups are attached to N-5 and/or N-10 of the tetrahydrofolate which carries the methyl groups to other compounds. The enzyme thymidylate synthase (TS) catalyzes transfer of the carbon from the tetrahydrofolate to the target molecules. In order to do so, TS must oxidize the folate ring of the tetrahydrofolate, which reverts it back into a dihydrofolate. For this process to repeat, cells must repeatedly use DHFR to reduce the dihydrofolate into the active tetrahydrofolate form. This requires continual DHFR activity.

Methotrexate inhibits the activity of DHFR by tightly, though reversibly, binding to it rendering it inactive. It enters the cell via specific folate receptors, the low pH folate transporter, or by reduced folate carriers. Once in the cell, methotrexate binds to DHFR. This binding reduces the amount of DHFR available to the cell, and stops the reduction of the tetrahydrofolate precursors, ie. folic acid and dihydrofolic acid. Without tetrandryofolate, the active folate, the cell cannot create new purine and thymidine nucleotides for DNA synthesis. Without replication, cell growth is blocked.

The toxicity of MTX is of use in its cancer therapeutic applications and in selecting cells based on their ability to grow in its presence, reflecting the level of amplification of the DHFR gene in the cells. However, according to the present invention MTX may be used as a marker compound (for example in a fluorescently-labelled form) and it is desirable to detect its binding to cells, particularly cells which express DHFR, without it causing toxic effects on DHFR-amplified cells. If MTX is used at a high enough concentration it may be toxic even in cells in which DHFR is expressed at a high level. In some embodiments the present invention may employ a pre-incubation with a marker compound such as MTX at a relatively low concentration in order to enrich for DHFR-amplified cells (see below), and at this stage MTX-induced toxicity is necessary in order to remove less productive cells. However at the stage when MTX (e.g. fluorescently-labelled MTX) is used to detect binding to DHFR, it may be necessary in some cases to use a high concentration of MTX in order to visualise binding to highly productive cells. At this stage it is not desirable to induce toxicity in the highly productive DHFR-amplified cells. Therefore in some embodiments, tetrahydrofolate may be included in the medium during incubation with MTX (e.g. fluorescently-labelled MTX), for example during incubation with MTX immediately prior to detection of MTX binding, in order to mitigate the effects of MTX-induced toxicity.

In one embodiment, the method of the present invention may comprise a step of pre-incubating the cells with the marker compound, e.g. exposing the cells to the marker compound in order to produce a population of cells in which a gene encoding the reference polypeptide (and also the polypeptide of interest) is amplified. The marker compound need not be labelled in this step. This step of enrichment in amplified cells may be performed prior to the step in which the marker compound, which may be labelled at this stage, is exposed to the cells in order to detect its association with cells producing the polypeptide of interest. For example, in one embodiment the cells are pre-incubated with methotrexate in order to provide a cell population in which DHFR and a polypeptide of interest are amplified. Cells are then exposed to fluorescently-labelled methotrexate and binding detected (e.g. by imaging) in order to select cells from the amplified population which produce DHFR and the polypeptide of interest at a high level.

In a further embodiment, the association between the marker compound and the reference polypeptide may be negative at the cellular level. For instance, the marker compound may be transported out of the cell by the reference polypeptide, rather than remaining bound to it. In these embodiments, cells which overexpress the reference polypeptide, e.g. via gene amplification, show reduced levels of binding to the marker compound. This is the opposite of the embodiments discussed above, where the marker compound remains bound to the reference polypeptide and thus accumulates in cells in which the marker gene is amplified (i.e. the association between the marker compound and reference polypeptide is positive).

One example of a reference polypeptide which can produce a negative association with a marker compound is P-glycoprotein (multiple drug resistance or MDR1). P glycoprotein is an example of an amplifiable selectable marker but is a broad-specificity ATP-dependent efflux pump which transports various cytotoxic drugs out of the cells in which it is expressed. Thus cells in which P-glycoprotein is amplified show reduced levels of drugs such as the lipophilic cytoxic agents adriamycin, colchicine and vincristine. In specific embodiments, these cytotoxic agents can be used as marker compounds in combination with P glycoprotein as reference polypeptide. Cells showing low levels of the marker compounds are then selected as producing high levels of the polypeptide of interest.

In certain embodiments, the reference polypeptide need not necessarily be an amplifiable marker. Although amplifiable markers are preferred, other selectable markers can also be used as the reference polypeptide provided that their expression is linked to that of the polypeptide of interest. Dominant selectable markers which have not been shown to be amplifiable include microbially derived antibiotic resistance genes, for example neomycin, kanamycin or hygromycin resistance. Further suitable reference polypeptides include other marker enzymes used in selection systems for mammalian hosts, as discussed in Maniatis supra, pgs 16.9-16.15. Co-transfection protocols employing two dominant selectable markers have also been described (Okayama and Berg, *Mol. Cell Biol,* 5:1136, 1985). Thus suitable reference polypeptides include glutamine synthase, thymidine kinase, aminoglycoside phosphotransferase, hygromycin B phosphotranferase, xanthine-guanine phosphoribosyl transferase or asparagine synthetase. Suitable inhibitors which bind to these enzymes and which can be used in the present invention as marker compounds are known in the art and/or are discussed in Maniatis, supra.

In further embodiments, the marker compound is associated with the reference polypeptide but does not bind directly to it. For example, the marker compound may indirectly provide an indication of expression of the reference polypeptide in the cell by binding to a further compound, the level of which can be correlated with that of the reference polypeptide. In one embodiment, the reference polypeptide is an enzyme and the marker compound binds to a substrate or product of the enzyme. Cells which express the reference polypeptide, and hence the polypeptide of interest, may show elevated levels of the enzyme product and consequently elevated levels of binding of the marker compound. In one example, the reference polypeptide is DHFR and the marker compound binds to tetrahydrofolate. Since tetrahydrofolate is a product of DHFR, tetrahydrofolate levels are higher in cells which express DHFR. In a further embodiment, the reference polypeptide is an endopeptidase and the marker compound (e.g. an antibody) binds to a cleaved peptide product of the endopeptidase.

Uses of Detection Method

The detection method may be used for picking a cell or cell colony which produces a polypeptide of interest, by assessing the amount of a reference polypeptide produced by the cell or cell colony and picking that cell or cell colony. It will also be clear that similarly the detection method may be adapted to assess the productivity of a cell or colony in producing a protein of interest, for example a hybridoma cell or cell colony in producing an antibody of interest. The productivity which is determined may be compared to a predetermined cut off point, and only those cells or colonies which meet or exceed that target may be chosen. Thus, the detection method may be employed in a method of selecting a productive cell or cell colony from a plurality of cells or cell colonies.

Label/Reporter/Signal

The marker compound is capable of being detected, preferably by emitting a signal. For this purpose, the marker compound may be labelled with a reporter molecule. A "signal", as used here, is any detectable event. The signal may be the generation of an enzymatic activity, such as protease activity, transcriptional activity or luminescence inducing activity. Preferably, however, the signal is emission or absorption of electromagnetic radiation, for example, light.

Fluorescent Label

In highly preferred embodiments, the signal is a fluorescent signal. Included are fluorescence, phosphorescence or other signals which involve the modulation of the intensity or frequency of emission or absorption of radiation, for example, a FRET signal (described in further detail below).

Preferably, the fluorescent signal is emitted from a fluorophore such as a fluorescent protein or fluorescent chemical. Thus, marker compound may comprise a reporter molecule comprising a fluorophore such as a fluorescent protein or fluorescent chemical.

Examples of fluorescent chemicals include allophycocyanine, phycocyanine, phycoerythrin, rhodamine, tetramethyl rhodamine, 7-nitro-benzofurazan rhodamine isothiocyanate, oxazine, coumarin, fluorescein derivatives, for example, FAM (6-carboxyfluorescein), TET (6-carboxy-4,7,2',7'-tetrachloro-fluorescein), (FITC) fluorescein isothiocyanate and carboxyfluorescein diacetate, as well as Texas Red, acridine yellow/orange, ethidium bromide, propidium iodide and bis-benzamide (commercially available from Hoechst under the trade name H33258).

Preferred fluorescent chemicals are fluorescein isothiocyanate, rhodamine and phycoerythrin, and preferred fluorescent proteins are Green Fluorescent Protein, Blue Fluorescent Protein, Cyan Fluorescent Protein, Yellow Fluorescent Protein and Red Fluorescent Protein. The fluorescent signal may be modulated by fluorescent resonance energy transfer (FRET).

Methods of conjugating fluorescent labels to various entities, including peptides, polypeptides and antibodies, are well known in the art.

The fluorescent signal may be emitted from a fluorescent polypeptide. Thus, the marker compound may comprise a reporter molecule comprising a fluorescent polypeptide.

Examples of fluorescent polypeptides and proteins include Green Fluorescent Protein (GFP) from *Aequorea victoria* and Red Fluorescent Protein (RFP) from *Discosoma* spp. Derivatives and variants of these proteins, such as Cyan Fluorescent Protein, Blue Fluorescent Protein, Enhanced Green Fluorescent Protein (EGFP; GFPmut1; Yang, T. T., et al. (1996) *Nucleic Acids Res.,* 24(22):4592-4593; Cormack, B. P., et al. (1996) *Gene,* 173:33-38.), Enhanced Blue Fluorescent Protein (EBFP), Enhanced Yellow Fluorescent Protein (EYFP; Ormö, et al. (1996) *Science,* 273:1392-1395), Destablised Enhanced Green Fluorescent Protein (d2EGFP; Living Colors Destabilized EGFP Vectors (April 1998) CLONTECHniques XIII(2):16-17), Enhanced Cyan Fluorescent Protein (ECFP), and GFPuv (Haas, J., et al. (1996) *Curr. Biol.,* 6:315-324) may also be used. These fluorescent proteins are available from CLONTECH Laboratories, Inc. (Palo Alto, Calif., USA).

The signal may be a luminescence inducing activity. It will be appreciated that as light is generated during luminescence, the signal may at the same time be a luminescence inducing activity and emission of electromagnetic radiation.

The signal may also be the generation of an enzymatic activity, for example, transcriptional activity. The marker compound may therefore comprise a polypeptide with an assayable enzyme activity. Where the enzyme activity comprises transcriptional activity, this may be detected by assaying the expression of a reporter gene such as CD4, by fluorescent antibodies and FACs for example.

The reporter may be attached, coupled, fused, mixed, combined, or otherwise joined to the marker compound. The attachment, etc between the reporter and the marker may be permanent or transient, and may involve covalent or non-covalent interactions (including hydrogen bonding, ionic interactions, hydrophobic forces, Van der Waals interactions, etc).

In preferred embodiments, the reporter is permanently, preferably covalently attached to the marker compound. In such preferred embodiments, the reporter is chemically coupled or cross-linked to the marker compound. Any of the various methods of chemical coupling which are known in the art may be employed for this purpose.

In certain embodiments, it may be desirable to include spacing means between the reporter and the marker compound. Such spacing means may suitably comprise linkers or spacers as known in the art. The purpose of the spacing means is to space the reporter and the marker, to avoid for example steric hindrance and to promote detection of the reporter and hence the marker. Accordingly, depending on the application, the use of shorter or longer spacers may be preferred.

The spacing means may comprise linkers or spacers which are polymers of differing lengths (the length of which may be controlled by controlling the degree of polymerisation). Numerous spacers and linkers are known in the art, and the skilled person will know how to choose and use these, depending on the application. The skilled person will also know what spacer length to use.

The spacers may be made for example of polyethylenglycol, PEG derivatives or polyalkanes or homo poly amino acids. Dextrans and dendrimers, as known in the art, may also be used. In particular, the linkers or spacers may comprise nucleotide polymers (nucleic acids, polynucleotides, etc) or amino acid polymers (proteins, peptides, polypeptides, etc).

Solid or Semi-Solid Media

In preferred embodiments, the cells are grown on the surface of or within solid or semi-solid media.

Growth of cells, particularly antibody secreting hybridomas, on such media enhances secretion, as described in Goding, J. W. 1980. Antibody production by hybridomas. [Review]. *J. Immunol. Methods.,* 39(4): 285-308, Sharon, J., Morrison, S. L. and Kabat, E. A. 1979. Detection of specific hybridoma clones by replica immunoadsorption of their secreted antibodies. *Proc. Natl. Acad. Sci.* (*USA*), 76(3): 1420-4 and Davis, J. M., Pennington, J. E., Kubler, A.-M. and Conscience, J. F. 1982. A simple, single-step technique for selecting and cloning hybridomas for the production of monoclonal antibodies. *J. Immunol. Methods.,* 50: 161-171.

Methylcellulose media may, for example, be obtained from Sigma-Aldrich Company Ltd (Dorset, UK) under catalogue number M0387 (Methyl cellulose viscosity 1,500 cP (2% aqueous solution, 20° C.) (lit.) CAS Number 9004-67-5) or catalogue number M0512 (Methyl cellulose viscosity 4,000 cP (2% aqueous solution, 20° C.) (lit.) CAS Number 9004-67-5).

In highly preferred embodiments, the polypeptide of interest is secreted from a cell or colony of cells grown on the surface of or within methylcellulose media. The use of methylcellulose media is well known in the art, and protocols have been established to enable hybridoma cloning on such media. See for example, the ClonaCell™-HY Hybridoma Cloning Kit Procedure Manual (StemCell Technologies, Vancouver, Canada), herein incorporated by reference.

The media may optionally comprise growth factors or other supplements optimized to support the selection and growth of the relevant cells. Where solid or semi-solid media are employed, in one embodiment the marker compound is included in the media to allow binding to take place. Alternatively the marker compound may be incubated with the cells before they are plated and overlaid with the solid or semi-solid media.

In some embodiments, the reference polypeptide or the polypeptide of interest may be secreted into the medium such that it surrounds the cell or colony to form a halo or aura. Thus, the halo or aura in general terms comprises a concentration of polypeptide in the immediate environs of the cell or colony.

Haloes or auras are particularly pronounced so where the cell or colony is growing on the surface of or within a solid or semi-solid medium. The halo or aura arises through the fact that diffusion of the secreted polypeptide away from the cell or colony producing it is restricted.

The halo or aura may be detected visually without any aids, or detection may be promoted by reaction with the marker compound. For example, where the marker compound is labelled with a signal generating reporter, the halo or aura may take the form of an area of signal surrounding the cell or colony. In particular embodiments, the label is a fluorescence label and the aura or halo comprises an area of fluorescence. Formation of such a halo or aura allows the detection of secreted polypeptide to be more easily detected.

The halo or aura may preferably be detected by a visualisation system in a robotic picking apparatus, for example.

Antibodies

In certain embodiments, the polypeptide of interest and/or the reference polypeptide may be an antibody. Moreover, the marker compound may be an antibody which binds to the reference polypeptide. An antibody which binds to the polypeptide of interest may also be used in a further step, if required, to confirm expression of the polypeptide of interest by a cell or cell colony selected on the basis of expression of the reference polypeptide.

Antibodies comprise immunoglobulin molecules. Immunoglobulin molecules are in the broadest sense members of the immunoglobulin superfamily, a family of polypeptides comprising the immunoglobulin fold characteristic of antibody molecules, which contains two β sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor). The methods described here may therefore make use of any immunoglobulin superfamily molecule which is capable of binding to a target molecule. Peptides or fragments derived from immunoglobulins may also be used.

Antibodies, as used herein, refers to complete antibodies or antibody fragments capable of binding to a selected target, and including Fv, ScFv, F(ab') and F(ab')$_2$, monoclonal and polyclonal antibodies, engineered antibodies including chimeric, CDR-grafted and humanised antibodies, and artificially selected antibodies produced using phage display or alternative techniques. Small fragments, such as Fv and ScFv, possess advantageous properties for diagnostic and therapeutic applications on account of their small size and consequent superior tissue distribution. Preferably, the antibody is a single chain antibody or ScFv.

The antibodies may be altered antibodies comprising an effector protein such as a toxin or a label. Use of labelled antibodies allows the imaging of the distribution of the antibody in vivo. Such labels may be radioactive labels or radioopaque labels, such as metal particles, which are readily visualisable within the body of a patient. Moreover, they may be fluorescent labels (such as the ones described here) or other labels which are visualisable on tissue samples removed from patients. Antibodies with effector groups may be linked to any association means as described above.

Antibodies to be used as marker compounds may be obtained from animal serum, or, in the case of monoclonal antibodies or fragments thereof, produced in cell culture. Recombinant DNA technology may be used to produce the antibodies according to established procedure, in bacterial, yeast, insect or preferably mammalian cell culture. The selected cell culture system preferably secretes the antibody product.

Growing of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, for example foetal calf serum, or trace elements and growth sustaining supplements, for example feeder cells such as normal mouse peritoneal exudate cells, spleen cells, bone marrow macrophages, 2-aminoethanol, insulin, transferrin, low density lipoprotein, oleic acid, or the like. The culture medium may be serum-free or animal-produce free, such as a chemically defined medium, in order to minimise animal derived contamination. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

Use of insect cells as hosts for the expression of proteins has advantages in that the cloning and expression process is relatively easy and quick. In addition, there is a high probability of obtaining a correctly folded and biologically active protein when compared to bacterial or yeast expression. Insect cells may be cultured in serum free medium, which is cheaper and safer compared to serum containing medium. Recombinant baculovirus may be used as an expression vector, and the construct used to transfect a host cell line, which may be any of a number of lepidopteran cell lines, in particular *Spodoptera frugiperda* Sf9, as known in the art. Reviews of expression of recombinant proteins in insect host cells are provided by Altmann et al. (1999), *Glycoconj J,* 1999, 16, 109-23 and Kost and Condreay (1999), *Curr Opin Biotechnol,* 10, 428-33.

In vitro production provides relatively pure antibody preparations and allows scale-up to give large amounts of the desired antibodies. Techniques for bacterial cell, yeast, insect and mammalian cell cultivation are known in the art and include homogeneous suspension culture, for example in an airlift reactor or in a continuous stirrer reactor, or immobilised or entrapped cell culture, for example in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) *Nature,* 256:495-497; U.S. Pat. No. 4,376,110; Harlow and Lane, *Antibodies: a Laboratory Manual,* (1988) Cold Spring Harbor, incorporated herein by reference. Techniques for the preparation of recombinant antibody molecules is described in the above references and also in, for example, EP 0623679; EP 0368684 and EP 0436597, which are incorporated herein by reference.

The cell culture supernatants are screened for the desired antibodies, preferentially by immunofluorescent staining of cells expressing the desired target by immunoblotting, by an enzyme immunoassay, for example a sandwich assay or a dot-assay, or a radioimmunoassay.

For isolation of the antibodies, the immunoglobulins in the culture supernatants or in the ascitic fluid may be concentrated, for example by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or immunoaffinity chromatography, for example affinity chromatography with the a protein containing a target or with Protein-A.

Antibodies generated according to the foregoing procedures may be cloned by isolation of nucleic acid from cells, according to standard procedures. Usefully, nucleic acids variable domains of the antibodies may be isolated and used to construct antibody fragments, such as scFv.

The methods described here preferably employ recombinant nucleic acids comprising an insert coding for a heavy chain variable domain and/or for a light chain variable domain of antibodies. By definition such nucleic acids comprise coding single stranded nucleic acids, double stranded nucleic acids consisting of the coding nucleic acids and of complementary nucleic acids thereto, or these complementary (single stranded) nucleic acids themselves.

Furthermore, nucleic acids encoding a heavy chain variable domain and/or for a light chain variable domain of antibodies can be enzymatically or chemically synthesised nucleic acids having the authentic sequence coding for a naturally-occurring heavy chain variable domain and/or for the light chain variable domain, or a mutant thereof. A mutant of the authentic sequence is a nucleic acid encoding a heavy chain variable domain and/or a light chain variable domain of the above-mentioned antibodies in which one or more amino acids are deleted or exchanged with one or more other amino acids. Preferably the modification(s) are outside the complementary determining regions (CDRs) of the heavy chain variable domain and/or of the light chain variable domain of the antibody. Such a mutant nucleic acid is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly yeast, bacterial or mammalian cells, to obtain an optimal expression of the heavy chain variable domain and/or a light chain variable domain.

The term mutant is intended to include a DNA mutant obtained by in vitro or in vivo mutagenesis of DNA according to methods known in the art.

Recombinant DNA technology may be used to improve antibodies. Thus, chimeric antibodies may be constructed in order to decrease the immunogenicity thereof in diagnostic or therapeutic applications. Moreover, immunogenicity may be minimised by humanising the antibodies by CDR grafting [European Patent 0 239 400 (Winter)] and, optionally, framework modification [European Patent 0239400; Riechmann et al., (1988) *Nature,* 322:323-327; and as reviewed in international patent application WO 90/07861 (Protein Design Labs)].

Recombinant nucleic acids may be employed comprising an insert coding for a heavy chain variable domain of an antibody fused to a human constant domain γ, for example γ1, γ2, γ3 or γ4, preferably γ1 or γ4. Likewise recombinant DNAs comprising an insert coding for a light chain variable domain of an antibody fused to a human constant domain κ or λ, preferably κ may also be used.

More preferably, CDR-grafted antibodies, which are preferably CDR-grafted light chain and heavy chain variable domains only, may be used. Advantageously, the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule. Such antibodies are known as ScFvs.

Antibodies may moreover be generated by mutagenesis of antibody genes to produce artificial repertoires of antibodies. This technique allows the preparation of antibody libraries, as discussed further below; antibody libraries are also available commercially. Hence, artificial repertoires of immunoglobulins, preferably artificial ScFv repertoires, are used as an immunoglobulin source.

Isolated or cloned antibodies may be linked to other molecules, for example nucleic acid or protein association means by chemical coupling, using protocols known in the art (for example, Harlow and Lane, *Antibodies: a Laboratory Manual*, (1988) Cold Spring Harbor, and Maniatis, T., Fritsch, E. F. and Sambrook, J. (1991), *Molecular Cloning: A Laboratory Manual.*, Cold Spring Harbor, N.Y., Cold Spring Harbor Laboratory Press).

Robotic Detection and Picking

In preferred embodiments, any of the steps set out in relation to the detection method, such as exposing the cells to a marker compound, detection of binding, as well as associated steps such as selection and/or picking of cells or colonies of interest may be conducted using automated robotic apparatus. In preferred embodiments, the robotic apparatus comprises a ClonePix FL apparatus (Genetix, New Milton, United Kingdom).

Features of a robotic apparatus which are advantageous for the performance of the methods described here, and which are present in the ClonePixFL apparatus, include any one or more of the following: cool white light illumination; up to 5 fluorescence combinations; high-resolution cooled CCD camera; ability to image at standard pixel resolution of 7 µm permitting fluorescent detection of colonies with as few as 10 cells; image zooming to 1 µm resolution for detailed colony inspection; ability to pick colonies at up to 400 clones per hour; easy-to-use custom software (ExCellerate) for intelligent picking, Halo Recognition, barcoding and clone-by-clone data tracking; stackers hold up to 10 source and collection plates, and optional Class II-type containment.

The ClonePixFL apparatus is described in detail below.

Figure 6:
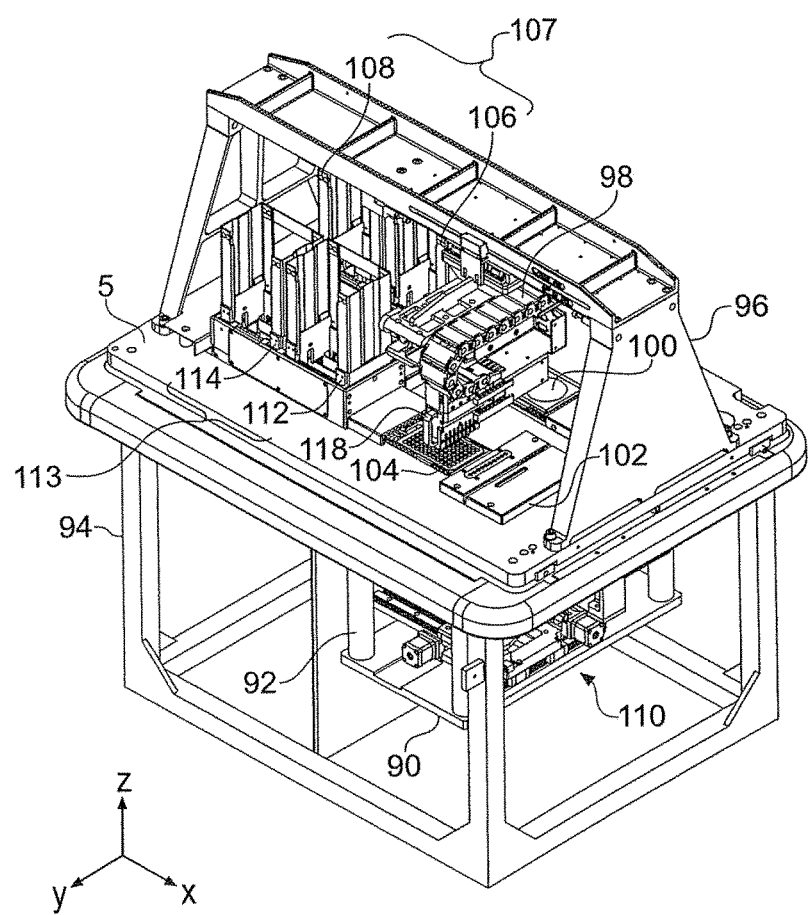
FIG. 6 is a perspective view of a robotic apparatus for carrying out methods according to the invention.

FIG. 6 is a perspective view of the ClonePixFL robotic platform for carrying out methods of the invention in an automated way. The apparatus may be considered to be a robot for picking, gel coring or other biological manipulation task with integrated fluorescence excitation and collection (i.e. detection) optics. The apparatus can be subdivided notionally into two half spaces existing above and below a main bed 5 which is supported by a frame 94.

Above the main bed 5, the apparatus appears as similar to a conventional picking robot. A cell picking head 118 is provided that comprises a plurality of hollow pins for aspirating animal cells. The cell picking head 118 is movable over the main bed 5 by a head position system made up of x- y- and z-linear positioners 98 connected in series and suspended from a gantry 96. A wash/dry station 102 is also provided on the main bed 5 for cleansing the pins. The whole upper half space of the apparatus will typically be enclosed in a housing (not shown) including a hinged door extending over one side and part of the top of the apparatus.

Below the main bed 5, an optics sub-assembly 110 is provided to accommodate fluorescence excitation and detection optics system which is mounted on a tray 90 suspended from the main bed 5 by pillars 92. The under-slung optics system is arranged to view containers such as Petri dishes and well plates placed on the imaging station 100.

In use in the performance of the detection method described in this document, a Petri dish or other container (not shown) containing cells or colonies producing polypeptides (some of interest) is placed on the imaging station 100. Such containers are referred to for convenience generically as "well plate"s in the following description, although it will be evident that they need not comprise wells. Thus, where the term "plate" or "well plate" is employed, it should be understood as encompassing any container suitable for growing cells, such as Petri dishes, microtitre dishes, 6 well plates, etc.

The main bed 5 is provided with two main working stations, namely an imaging station 100 and a replating station 104, each of which is positioned at the end of a respective well plate feed lane. Each well plate feed lane has a well plate feeder/stacker. The well plate feeder/stacker 107 for the imaging station 100 has a well plate feed storage cassette 106 and well plate (re-)stack storage cassette 108. A stack of well plates are held in the feed storage cassette 106, fed in turn down the lane via a delidder (not shown) to the imaging station 100, returned back along the lane, relidded and passed into the rear storage cassette 108. A similar well plate feeder/stacker 113 is used for the other lane to supply well plates from the storage cassette 112 to the replating station 104 and back along the lane to the (re-)stack storage cassette 114.

The well plate feeder/stacker mechanisms including delidding are described fully in EP-A-1 293 783, the contents of which are incorporated herein by reference.

It should be noted that although the description above refers the term "well plate" in the description of the "well plate feed lane at the end of the imaging station 100", the "well plate feeder/stacker 107" and the "well plate feed storage cassette 106", the term "well plate" should be taken as limiting to a container with wells. Instead, it should be treated as a generic description of any container capable of containing cells to be picked. In the performance of the detection method described herein, for example, it will be preferable to use Petri dishes or other flat dishes for growing cells producing polypeptides to be picked. Accordingly, such dishes may be used in the apparatus described with appropriate minor modifications, if necessary.

The cell picking head 118 can thus be moved from the imaging station to the replating station to allow replating of animal cells from a target well plate to a destination well plate. The arrangement described above enables a plurality of target plates, each containing cells or colonies expressing polypeptides to be picked, in containers such as Petri dishes, to be processed at the imaging station 100 in turn. The picked cells or colonies are plated onto destination well plates at the replating station 104.

In the illustrated embodiment, there is only one destination lane. However, it may be desirable in some cases to have 2, 3 or 4 destination lanes. This may be useful when it is desired to split the animal cells from a given target well into multiple destination wells. The feeder/stacker mechanism is fully modular, so the number of well plate feed lanes can be increased without difficulty.

Figure 7:
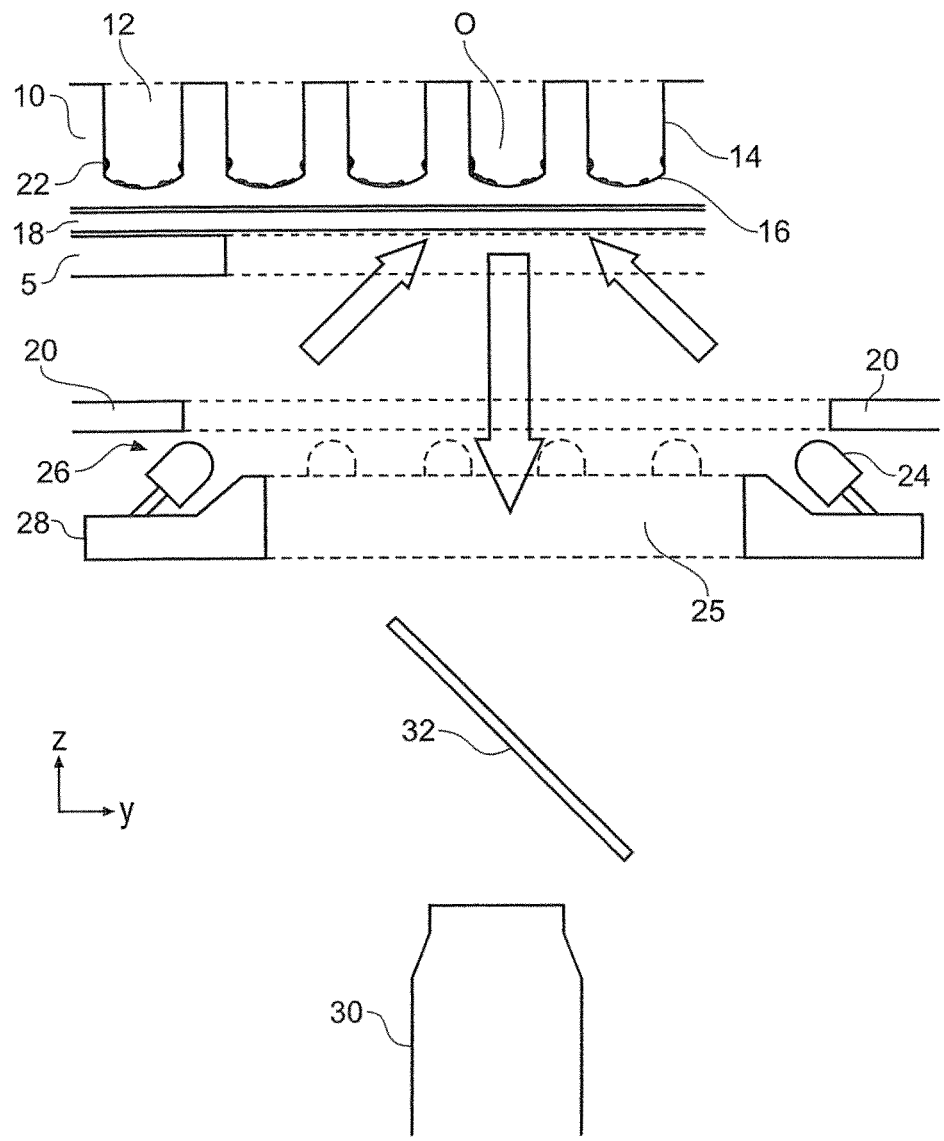
FIG. 7 is a schematic sectional side view showing the sample excitation and collection paths in the vicinity of the sample using a well plate as an example sample container.

FIG. 7 is a schematic sectional side view showing principles of the design of the optical sub-assembly 110. Part of a well plate 10 showing 5 wells is also shown. Adherent colonies 22 have been cultured in the wells also as shown, the colonies forming around the base 16 and lower sidewalls 14 of the wells 12. It will be appreciated that samples in other containers may also be studied, such as Petri dishes described above. In such containers, particularly those which contain semi-solid media such as methylcellulose, cells and colonies are growing in the media.

The imaging station is formed in an aperture in the main bed 5 covered by a sheet of optically transparent material, typically glass, that forms a light table 18. For optical analysis, a well plate 10 is arranged on the light table 18 as shown, having been deposited there by the well plate feeder/stacker. The apparatus is designed to image one well at a time. To image a specific well 12 of a well plate, the optical sub-assembly 110 is aligned relative to the well 12.

The optical sub-assembly 110 comprises two illumination sources and a collection part.

The first illumination source is formed of a plurality of white light emitting diodes (LEDs) 24 arranged to form an LED ring 26 located in a collar 28 with a central aperture 25 with the optical axes of the LEDs lying on the surface of a common cone, the point of which is coincident and labeled as the object position O in the figure. This white light source is provided principally to collect conventional images of the sample, for example as are used for performing cell confluence detection by image processing techniques. An apertured top plate 20 lying above the LED ring 26 is also illustrated. This is a structural component and has no significance for the optical design.

This second illumination source (not shown in this figure) is arranged to illuminate from the side, as shown by the sideways arrow, onto a semi-silvered mirror 32 which deflects the excitation light vertically onto the sample, as shown by the upwardly pointing arrow, in order to perform fluorescence measurements.

The collection part of the optical sub-assembly is made up of a zoom lens 30 with autofocus and is used to collect light when either (or both) of the illumination sources is used. The optical axis is vertical and coincident with the object position O.

The well to be imaged is thus aligned laterally with the optical axis of the collection optics and the fluorescence excitation optics and laterally and vertically with the center point of the white light lateral illumination, whereby the center point of the lateral illumination is around the base of the well or slightly higher as illustrated. The LEDs 24 thus illuminate a well 12 arranged in the object position O at an oblique angle from below so that an image of the well 12 is taken in a dark field configuration where light from the LEDs, if not scattered, does not contribute to the well image gathered by the collection lens 30.

Figure 8:
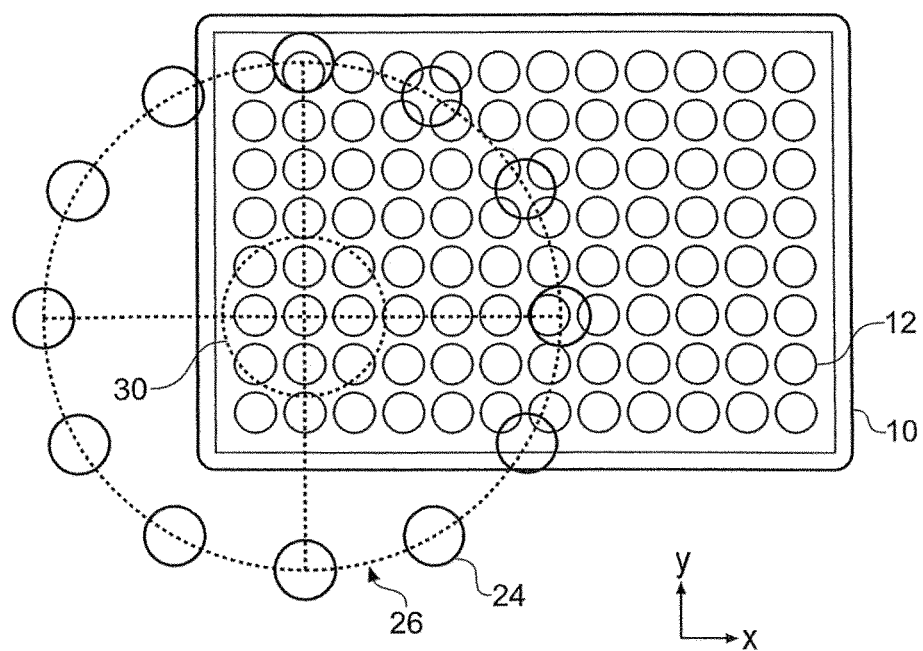
FIG. 8 is a schematic plan view of the sample vicinity with a well plate as the sample container.

FIG. 8 is a schematic plan view of selected parts of the optical system shown in FIG. 7. The well plate 10 is a 96 well version and is shown aligned with the optical sub-assembly 110 so that a well 12 three rows up (row m=3) and two columns along (column n=2) is targeted, as illustrated by the objective lens 30 and LED ring 26 of LEDs 24. The optical sub-assembly is arranged on x- and y-positioners so that the collection lens 30 and illumination ring 26 can be moved together to image any one of the wells 12. Typically, the wells will be imaged in sequence row-wise and column-wise with a rastering process. This is achieved by moving the optical sub-assembly while the well plate remains static which is preferable so that liquid in the wells is not shaken by moving the well plate between imaging each well which might have an adverse influence on the imaging.

It will be appreciated that the ability of the apparatus to image a growing container comprising a single well may be extended to enable imaging of a growing container of any suitable size. Thus, samples in other (larger) containers may also be studied, such as Petri dishes described above suitable for use in the detection method described in this document. In such dishes, the cells or colonies will be scattered more or less randomly across the surface of the plate, instead of being arranged in a row/column configuration. Nevertheless, the x- and y-positioners do not restrain the collection lens 30 and illumination ring 26 to movement in a discrete fashion, but these are instead movable continuously across the surface of the plate. Accordingly, the x- and y-positioners enable any portion of the plate to be imaged by the collection lens 30 and illumination ring 26.

Figure 9A:
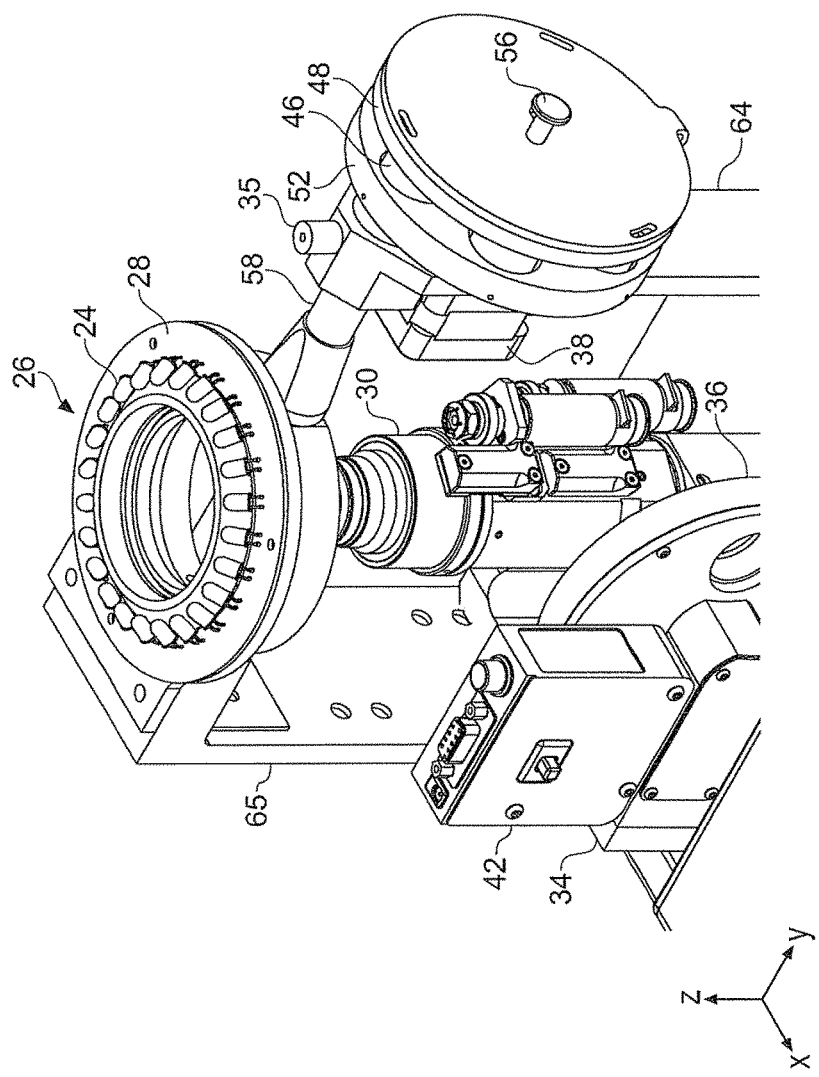
FIGS. 9A, 9B and 9C are perspective and orthogonal side views of the optics sub-assembly arranged below the main bed of the apparatus of FIG. 6.
Figure 9B:
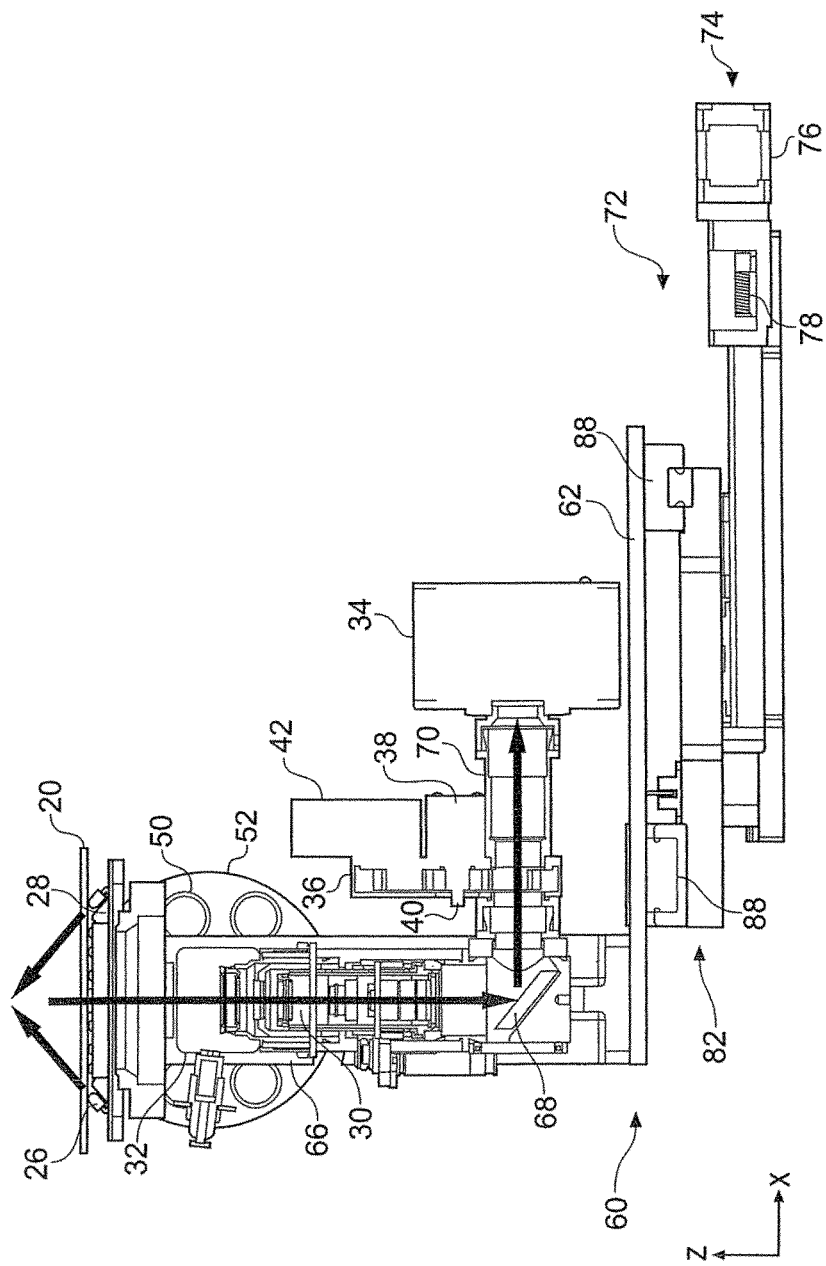
Figure 9C:
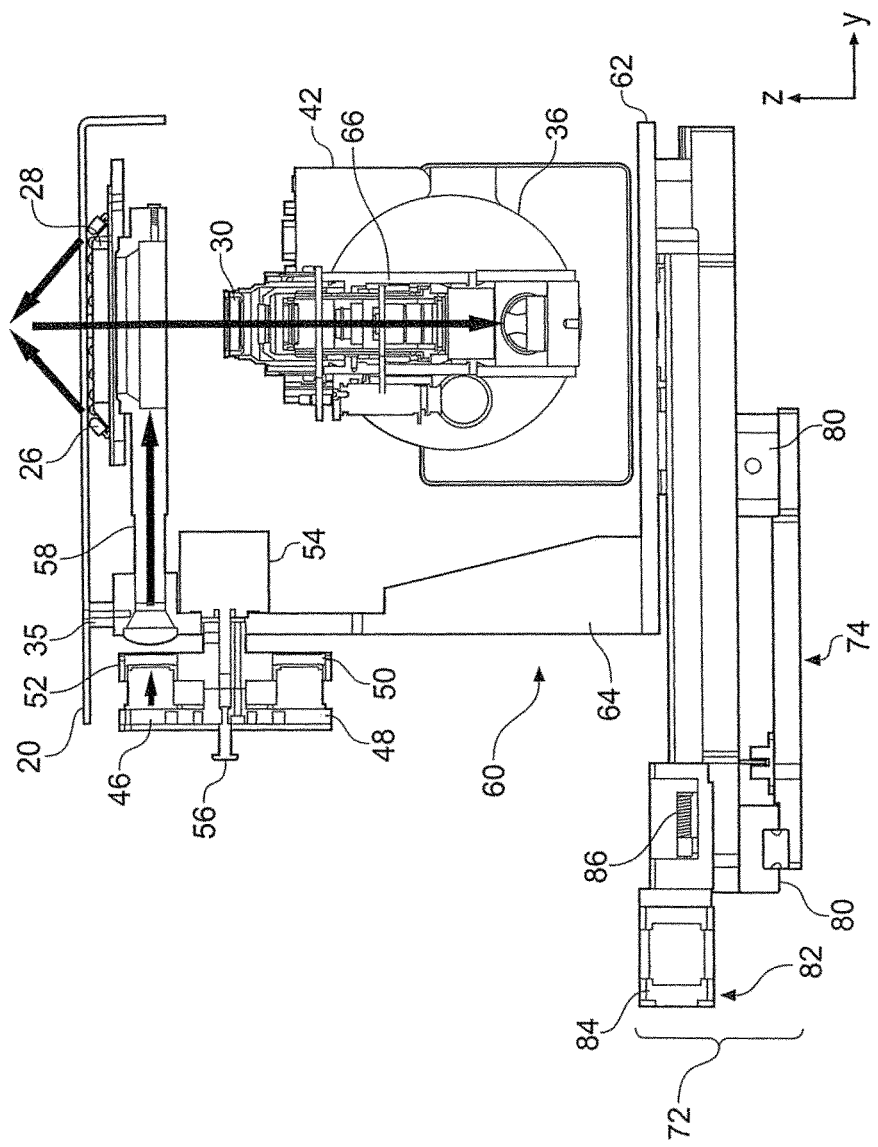

FIGS. 9A, 9B and 9C are perspective and orthogonal side views of the optics sub-assembly arranged below the main bed of the apparatus of FIG. 6. These three figures are described together, rather than in turn, since they are different views of the same equipment, noting that not all features are visible or marked with reference numerals in each figure.

The previously described collar-mounted LED ring 24, 26, 28 is evident in all three figures. The LED collar 28 is cantilevered out on a side bracket from a vertical mounting plate 65 (FIG. 9A) which is part of a frame 60. The vertical mounting plate 65 is upstanding from a base plate 62.

The fluorescence excitation optics is mounted on the base plate 62 via a further vertical mounting plate 64. The excitation source is colored LEDs 44 (not shown) that are arranged in groups of different colors 46 on a wheel 48 which is a converted filter wheel with LED groups 46 arranged at each filter position. In front of each LED group 46 there is a bandpass or other suitable narrowband filter 50 (see FIGS. 9B & 9C) each arranged in the filter position of a further filter wheel 52 arranged coaxially and on the same motor spindle 56 as the filter wheel 48, the two wheels being driven in unison by a motor 54. Each bandpass filter 50 is selected to transmit a range of wavelengths matched to the emission wavelength band of the LED group 46 with which it is paired. Light from the uppermost LED group 46 is directed horizontally through a light pipe 58, which is not a waveguide, merely a shroud for preventing light spillage, onto the semi-silvered mirror 32 (see FIG. 9B and also FIG. 7) which serves as a beam splitter for directing a portion of the colored LED light through the LED collar's aperture 25 to the object position. Other forms of beam splitter could also be used, for example a cubic beam splitter. The beamsplitter is preferably removable, or movable away from the aperture 25 so that when lateral illumination from the colored LED groups is not needed, it can be taken out of the collection path so that it does not result in loss of collected signal. A mounting stub 35 is also evident in FIGS. 9A and 9C. This mounting stub 35 is for connecting the colored LED group features to the top plate 20 (removed in FIG. 9A, but shown in FIGS. 9B and 9C and also FIG. 7).

The collection lens 30 is held vertically in a mounting tube 66 (see FIGS. 9B & 9C) at the base of which is arranged a plane deflecting mirror 68 which redirects the collected light horizontally and supplies it along a light pipe 70 to a CCD camera 34. Part way along the light pipe 70 there is arranged a filter wheel 36 mounted on a spindle 40 and driven by a motor 38. Drive electronics for the filter wheel 36 are housed in a unit 42. Typically filters will be used in the collection optics to filter out excitation light from the colored LED groups 46 when spectroscopic measurements are being performed. Collection side filters 45 may also be useful for filtering out fluorescence, e.g. to stop fluorescence from swamping out contrast of the cell periphery. This might be auto-fluorescence or fluorescence from a tag. For straightforward confluence detection using the white LEDs 24, no filter may be needed on the collection side.

The optical components are thus all mounted directly or indirectly on the base plate 62. The base plate 62 is carried by a linear positioner 82 which is in turn carried by a linear positioner 74 to provide xy-motion for the whole optical set-up. In the illustration, the x-positioner 74 is at the bottom with the y-positioner mounted on top of it. However, it will be appreciated this choice is arbitrary. It will also be appreciated that a parallel mechanism xy-positioner could be provided instead of two piggy-backed linear positioners. The x-positioner 74 comprises a motor 76, lead screw 78 and a pair of sets of guide bearings 80. The y-positioner 82 is the same, comprising a motor 84, lead screw 86 and a pair of sets of guide bearings 88.

As an alternative to having colored LED of different colors arranged in filter positions on a filter wheel as described above, it is possible to have concentric rings of different colors of LED in a single mounting. For example, the white light LED ring could be exchanged or supplemented with a number of LED rings of different colors. In principle an arbitrary arrangement of LEDs of different colors would provide the same functionality so long as LEDs of different colors could be driven independently, but would be a less elegant design. It would also be possible to use a single group of broadband LEDs in combination with filtering. However, this approach would tend to provide less illumination power than using different colors of LED. It will also be appreciated that other optical sources could be used including superfluorescent LEDs or diode lasers. Fixed wavelength or tunable diode lasers may be used.

By way of example, the table below gives, for a number of useful dyes, suitable LED types for the excitation LED groups 46 together with suitable pairs of excitation side filters 50 and collection-side (i.e. emission) filters 45. The peak excitation and emission wavelengths λ of the example dyes are also stated.

fluidics unit 186 which is controlled by the fluidics control unit 184 connected to the PC 130. The fluidics control unit 184 is used to control the pressure in the fluid lines to allow aspiration, retention and expulsion of liquid from the sample. The fluidics control unit 184 also controls the wash cycle of the pins and fluid lines, whereby cleaning fluid from the baths is aspirated and expelled from the ends of the pins during the cleaning cycle. A feeder/stacker control unit 145 is also provided for the feeder/stacker units, including the plate supply lanes, and is connected to the PC 130. Separate units 145 may be provided for each lane in view of the modular nature of the feeder/stacker assemblies. The figure also illustrates schematically an optional feature whereby a carrier in the form of a platen 146 is provided to carry one or more plates 10 or other biological sample containers. The platen 146 is movable in the x- and y-directions by associated motors 147 and motor controller unit 148 which is connected to the PC 130, these elements collectively forming a positioning system for plates or other containers arranged on the apparatus. The platen can then be moved in a controlled fashion to allow iterative scanning by the optical system across all wells of a plate. The platen may be provided with an integral heating element, so that plates or other biological sample containers carried by the platen can be maintained at elevated temperatures, for example to promote enzymatic activity in the samples.

| Dye | Peak Excitation λ (nm) | Peak Emission λ (nm) | LED Type | Excitation Filter | Emission Filter (Chroma Co.) |
|---|---|---|---|---|---|
| BFP | 381 | 445 | UV | none | D460/50m |
| CFP | 434 | 477 | Royal Blue | D(HQ)450/50X | D505/40m |
| EGFP | 488 | 507 | Blue | D(HQ)470/40X | HQ535/50m |
| FITC | 490 | 525 | Blue | D(HQ)470/40X | HQ535/50m |
| YFP | 513 | 527 | Cyan | D(HQ)500/30X | D550/40m |
| Rhodamine | 550 | 573 | Green | D(HQ)530/30X | HQ590/50m |
| DSRed | 565 | 582 | Green | D(HQ)530/30X | HQ590/50m |
| Cy5 | 649 | 670 | Red | D(HQ)623/36X | HQ700/75m |

Figure 10:
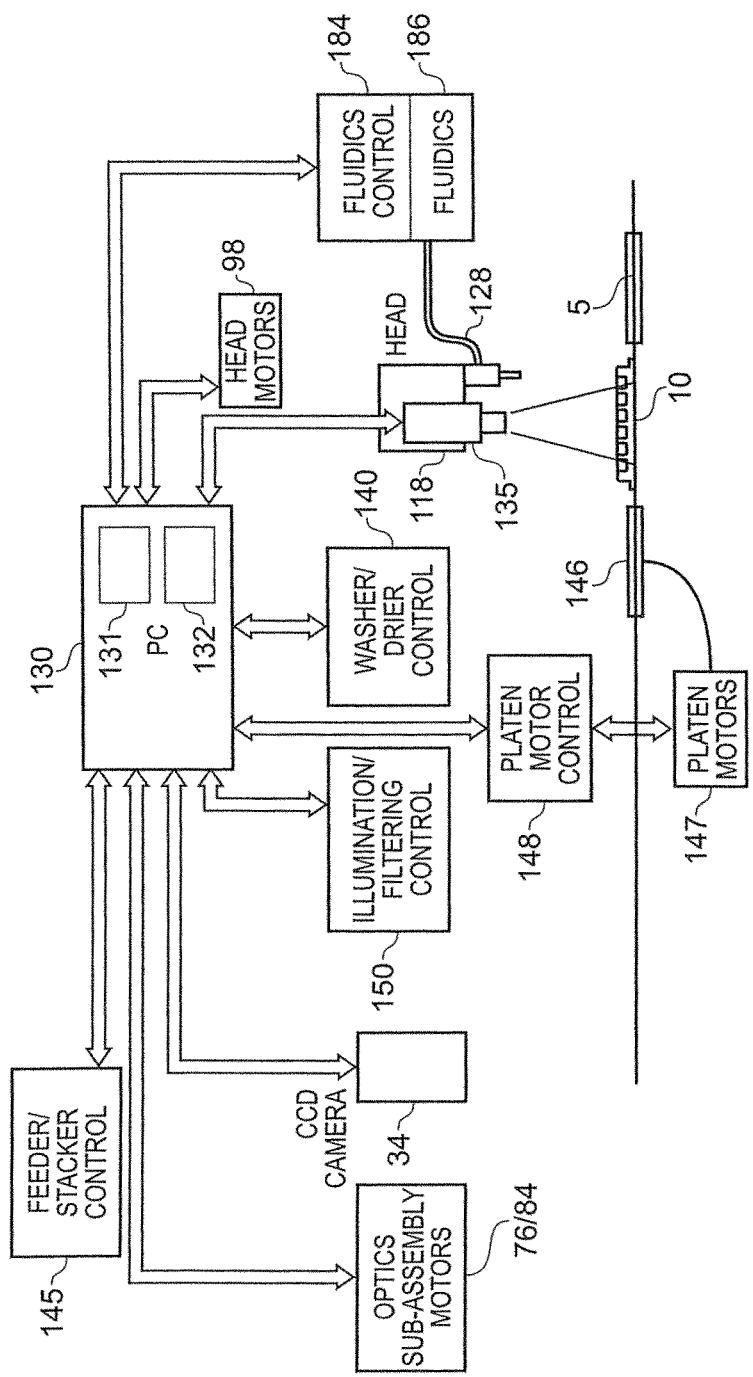
FIG. 10 is a block schematic diagram showing the control system of the apparatus.

FIG. 10 is a block schematic diagram showing the control system of the apparatus for coordinating the various components to perform the processes described above. A computer (PC 130) is used as the principal control component and is connected by electronic links using standard interfacing protocols to the various components that are part of the automated control system. The control is effected by control software 131 resident in the PC 130. Image processing and spectroscopic analysis software 132 is also resident in the PC 130 and linked to the control software 131. The image processing and spectroscopic analysis may also be carried out in hardware or firmware if desired. The CCD camera 34 is connected to the PC 130 for receiving digital images captured by the camera 34. An illumination and filter controller 150 is connected to the PC 130 for controlling the various under-bed optical sources and filter wheels of the optical sub-assembly 110. A washer/drier controller 140 is connected to the PC 130 and used to control the blower and the halogen lamps of the wash/dry station 102. The positioners 98 for moving the head 118 are connected to the PC 130. The PC 130 is also connected to the motors 76 and 84 of the x- and y-positioners of the under-bed optics sub-assembly 110. A head-mounted camera 135 is also provided for machine vision, such as bar-code detection on plates, and is connected to the PC 130 for receiving digital images captured by the head-mounted camera 135. These are used for aligning the pins of the head with the various locations of interest such as the wash/dry station 102, plates etc. The fluid lines 128 are connected to the It will thus be appreciated that lateral positioning can be achieved in a variety of ways either by moving the optical source and detector on a common platform under the bed of the apparatus, moving the sample with its own xy-positioning system on the sample carrier, or by moving the head. In any given apparatus or process, various combinations of these motion systems may be used.

In summary, the described robotic apparatus has a sample manipulation head with associated positioning system mounted above the main bed of the apparatus, and can be used for picking of cells, in particular animal cells, or for other biological or chemical applications. An imaging station is arranged on the main bed where a sample container containing a sample can be placed in an object position. Both excitation and collection optical sub-systems are mounted under the main bed of the apparatus for performing spectroscopic analysis on a sample at the imaging station. The integration is based on a reflection mode optical solution, which allows all the optical components to be mounted under the main bed of the apparatus. Consequently, ancillary software driven or manual processes can be carried on with whether or not spectroscopic measurements are being made.

However, it will be appreciated that methods according to the invention can be performed on different apparatus than described herein. In particular, imaging tasks can be carried out in a conventional stand-alone imager, such as a Fuji LAS-1000, and picking tasks with a conventional picking robot, such as a Genetix QPix.

EXAMPLES

Example 1

Detection of DG44 Cells in which DHFR and Therapeutic Antibody Gene Copy Number have been Amplified by Pre-Incubation with Methotrexate, Wherein Detection of DHFR is Achieved by Association with Fluorescein-Conjugated Methotrexate CHO DG44 cells were stably transfected with an expression vector encoding a therapeutic antibody (IgG1 against a bacterial protein) and DHFR. The cells were then incubated in the presence of varying concentrations of MTX as previously described in order to enrich for cell lines in which the DHFR gene has been amplified. Two cell lines (referred to as Cell line 1 and 2) were selected. Cell line 1 had been incubated in the presence of a final concentration of 50 nM MTX whereas Cell line 2 had been incubated with 150 nM MTX. The growth selection had taken place over a period of 4 months. These cells were then incubated without MTX for 1 week.

Cells from Cell line 1 and Cell line 2 were then seeded at $2 \times 10^5$ cells in a 24 well plate in Genetix Clone XP cell cloning media and 5% Foetal Bovine Serum. Varying concentrations of fluorescein-conjugated methotrexate (F-MTX, methotrexate conjugated to fluorescein isothiocyanate (FITC)) were added to different wells (0, 50, 150, 300, 600 and 1000 nM) and the cells incubated for 24 hours. The cells were then removed to an eppendorf tube and washed twice with PBS. Fresh media without MTX was added and the samples left on ice.

200 µl of each sample was then placed into a 96 well plate. The remaining cell samples were re-incubated in a 24 well plate. Fluorescent and brightfield images of each plate were then captured using an automated imaging device. The results are shown in FIGS. 1 and 2.

Figure 2:
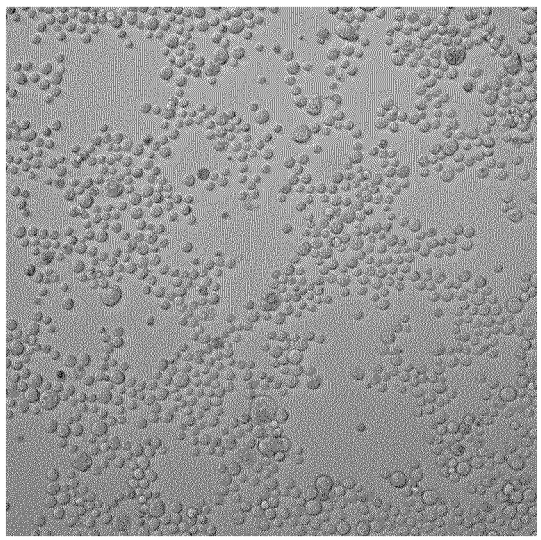
FIG. 2 shows brightfield images (panels A and C) and fluorescent images (panels B and D) of DHFR-amplified CHO DG44 cells which have been incubated in the presence of 600 nM (panels A and B) or 1000 nm (panels C and D) different concentrations of fluorescein-conjugated methotrexate.
Figure 2:
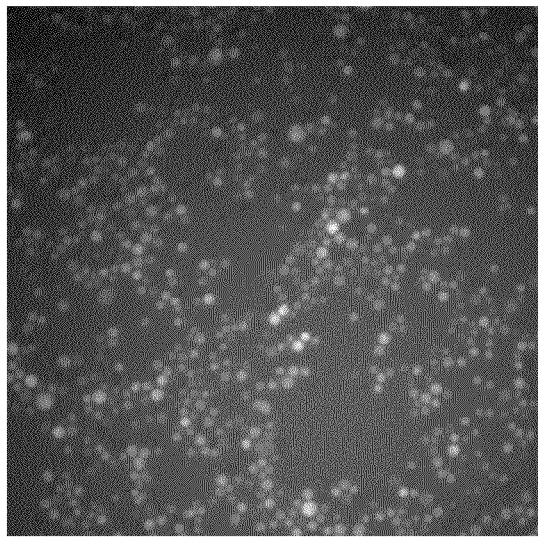
Figure 2:
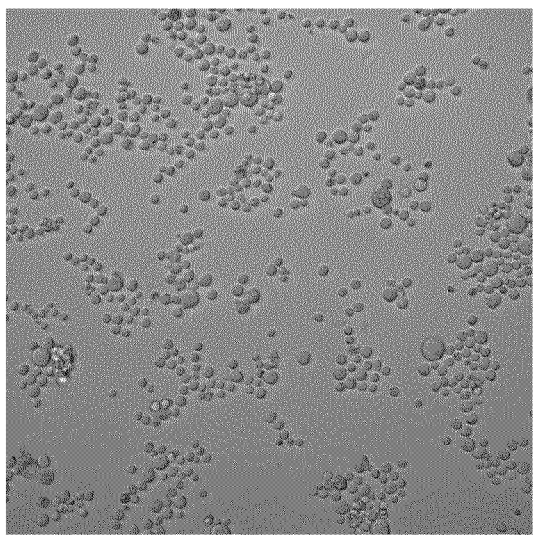
Figure 2:
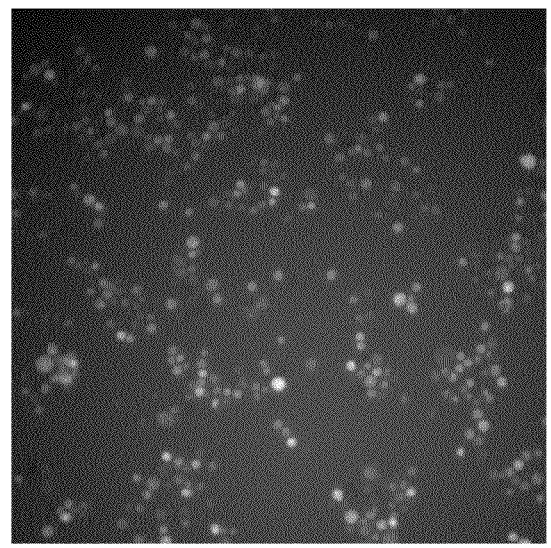

FIGS. 1 and 2 show brightfield (A, C) and fluorescent (B, D) images of cells from Cell line 1 which had been incubated in the presence of the following concentrations of F-MTX: 0, i.e. no F-MTX control (FIG. 1A, B); 150 nM (FIG. 1C, D); 600 nM (FIG. 2A, B); and 1000 nM (FIG. 2C, D). Similar results were obtained for Cell Line 2.

The results demonstrate that individual cells show varying levels of fluorescence corresponding to their F-MTX content, which corresponds to DHFR levels. Imaging of the cells using fluorescent light allows individual cells having a high DHFR content to be identified. These cells can be selected and picked for further use as high antibody-producing cell lines. Increasing F-MTX concentration between 150 nM and 1000 nM increased the overall cellular fluorescence levels, indicating that at low concentrations DHFR binding of F-MTX is not saturated.

Example 2

Detection of DG44 Cells in which DHFR and Therapeutic Antibody Gene Copy Number have been Amplified by Pre-Incubation with Methotrexate, Wherein Detection of DHFR is Achieved by Association with Fluorescein-Conjugated Methotrexate In this example, F-MTX binding to DG44 cells was analysed using a similar method to that described in Example 1. However, in Example 2 following incubation with F-MTX the cells were incubated for 15 minutes with fresh media (without F-MTX) to allow any unbound F-MTX to leave the cells. The standard wash with PBS then followed before imaging. In addition, the concentrations of F-MTX used were 0, 750 nM, 1000 nM and 2000 nM. Samples were removed before washing the pellet to determine the background level of F-MTX in relation to the specific fluorescence in the cells.

Figure 3:
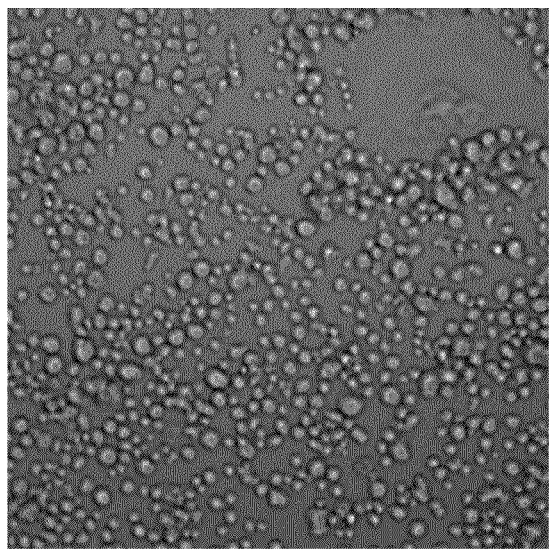
FIG. 3 shows brightfield images (panels A and C) and fluorescent images (panels B and D) of DHFR-amplified CHO DG44 cells which have been incubated in the presence of 750 nM (panels A and B) or 1000 nm (panels C and D) different concentrations of fluorescein-conjugated methotrexate.
Figure 3:
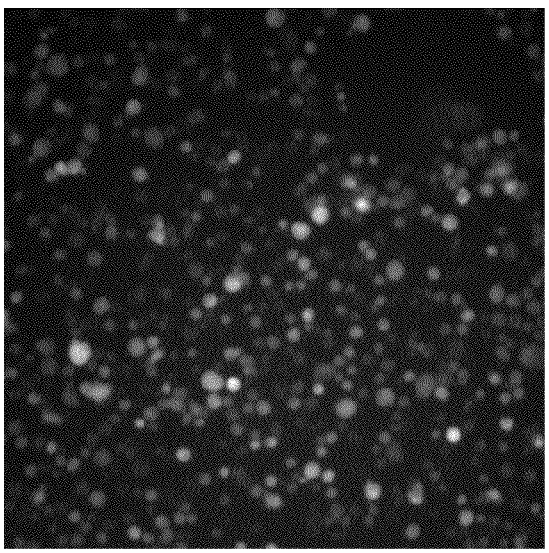
Figure 3:
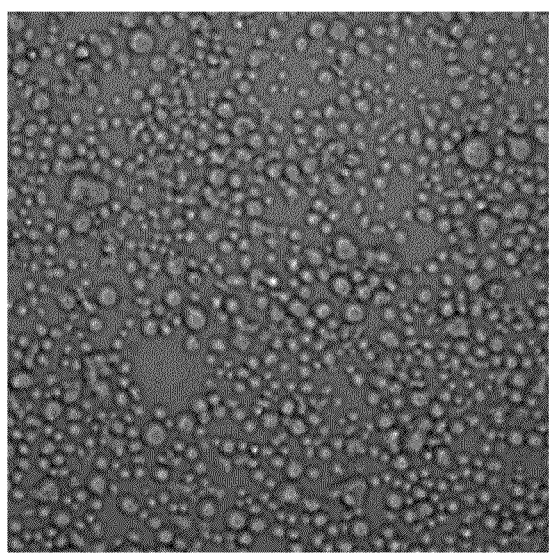
Figure 3:
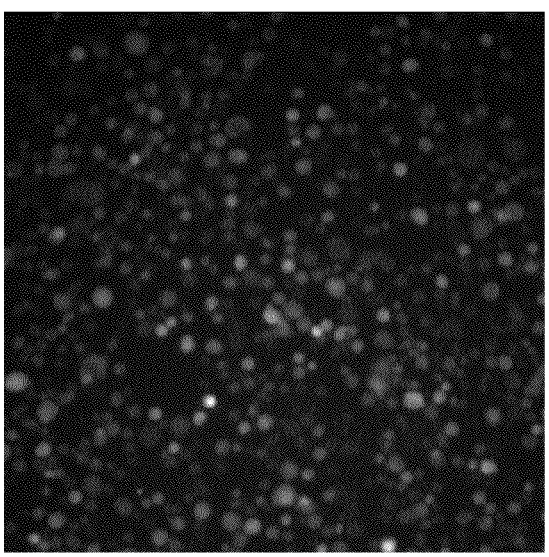

FIG. 3 shows brightfield (A, C) and fluorescent (B, D) images of cells from Cell line 1 which had been incubated in the presence of the following concentrations of F-MTX: 0.75 µM (FIG. 3A, B); and 1 µM (FIG. 3C, D). Similar results were obtained for Cell line 2, at the other concentrations of F-MTX tested and when no wash step was used.

The distribution of fluorescence between the 0.75 µM to 2 µM F-MTX conditions in each cell line does not appear to change significantly. Combining this with the results from the previous experiment suggests that binding of F-MTX to DHFR is saturated between 0.6 and 0.75 µM F-MTX. This suggests that the assay can be performed in semi-solid media because cells could be incubated with a low level of MTX without viability problems.

Samples had been taken for imaging before washing to determine whether the background or un-bound F-MTX would be visualised. However the background fluorescence did not hinder visualisation of the labelled cells. A similar range of cells was detected in the unwashed and washed conditions, suggesting the fluorescence was specific to high DHFR producing cells.

Example 3

Comparison of F-MTX Binding to DHFR-Amplified Cells and Cells Showing Basal DHFR Expression DHFR is expressed naturally in many cell types and therefore in this example F-MTX binding to DHFR-amplified cells was compared to F-MTX binding to a cell line in which DHFR is not amplified. CHO K1SV cells were chosen as the cell line showing basal DHFR expression, and were compared to CHO DG44 cells exposed to MTX as described above.

K1SV and DG44 cells were centrifuged and resuspended in MTX-free media, Genetix Clone XP media and 5% Foetal Bovine Serum. The cells were then seeded at $2 \times 10^5$ cells and incubated for 48 hours. Cells were spun again, resuspended in media containing FITC-MTX and incubated for 24 hours. After washing twice in PBS, cells were resuspended in MTX-free media and incubated for 60 minutes before imaging. The results are shown in FIG. 4.

Figure 4:
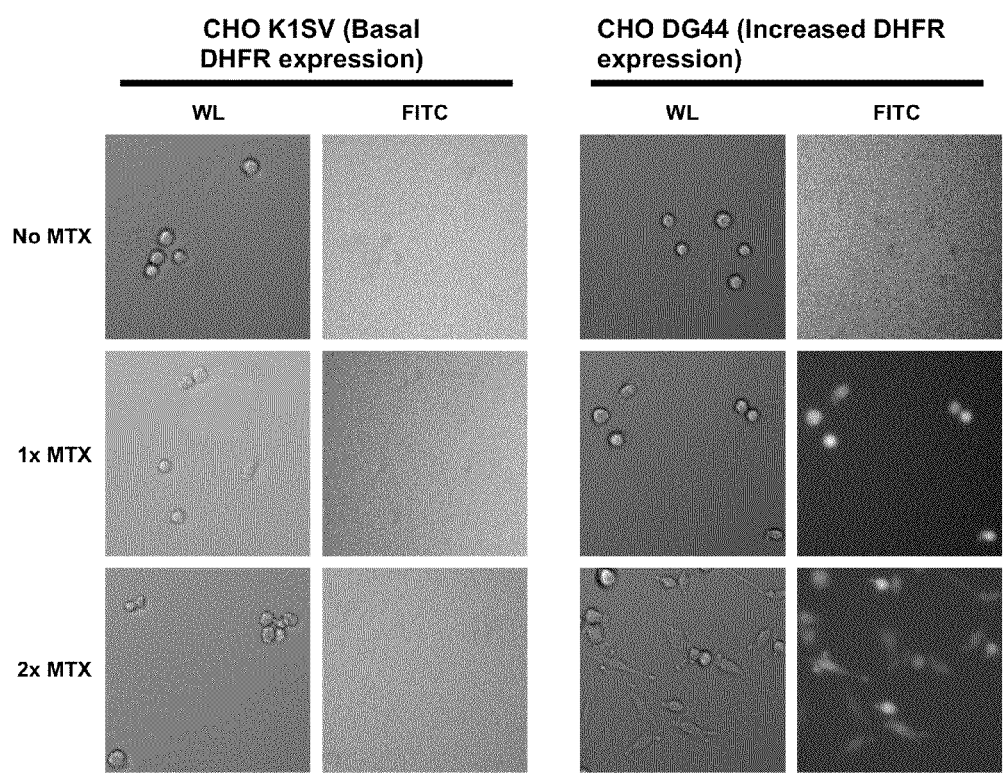
FIG. 4 shows brightfield and fluorescent images of CHO K1SV (expressing DHFR at basal levels) and CHO DG44 cells (in which DHFR has been amplified) exposed to varying concentrations of fluorescein-conjugated methotrexate.

FIG. 4 shows brightfield (WL) and fluorescent (FITC) images of K1SV and DG44 cells exposed to F-MTX. Cells were exposed to no F-MTX, or to 1 µM (1×MTX) or 2 µM (2×MTX) F-MTX. The results show that in K1SV cells, where DHFR is expressed only at basal levels, there was no detectable cell-associated F-MTX binding. In contrast, in DG44 cells in which DHFR has been amplified, cells showing increased DHFR expression can be identified by fluorescence associated with F-MTX binding.

Example 4

Correlation Between F-MTX Binding and Therapeutic Antibody Production in DG44 Cells In this example, anti-IgG antibodies were used to detect the therapeutic antibody which is co-amplified together with DHFR. DG44 (DHFR amplified) or K1SV (basal DHFR expression) cell preparations were incubated with F-MTX (0, 150 nM, 500 nM, 1 µM, 2 µM, or 3.6 µM) for 4 hours. The cells were washed with PBS then overlaid with semi-solid media. Anti-IgG antibodies labelled with a rhodamine fluorescent marker (Clone Detect AF594 or AF649) were included in the media to identify cells in which both the therapeutic antibody and DHFR are amplified. The results are shown in FIG. 5.

Figure 5:
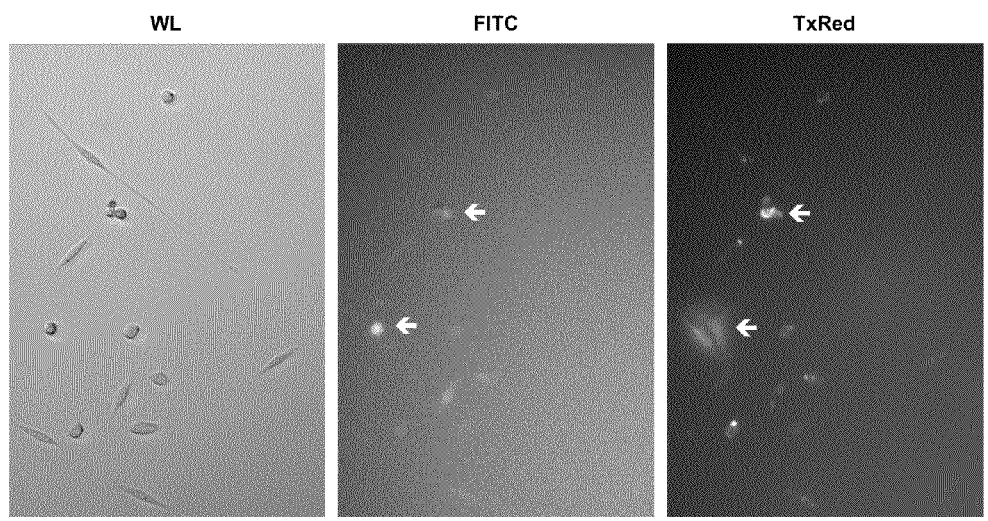
FIG. 5 shows images of CHO DG44 cells in which DHFR is amplified under brightfield or 2 different channels of fluorescent illumination.

FIG. 5 shows images of CHO DG44 cells in which DHFR is amplified under brightfield (WL) or fluorescent (FITC=fluorescein channel, TxRed=rhodamine channel) illumination. The FITC and rhodamine channels substantially overlapped in cells which had been incubated in F-MTX, indicating that high DHFR expression coincided with high antibody secretion (see arrows in FIG. 5).

The results presented in Examples 1 to 4 above demonstrate that cells previously exposed to MTX, as a means of selecting for high DHFR and therapeutic antibody gene copy number, can survive a 24 h incubation with a very high concentration of fluorescein-conjugated MTX. The cells had been selected originally in up to 0.15 µM MTX and survived incubation with up to 2 µM F-MTX with no significant problems.

The F-MTX bound to the DHFR was able to be visualized using fluorescent imaging devices, such that differences could be seen between the cells. The DHFR in the cells appears to be saturated at around 0.75 µM F-MTX concentration and can be visualized clearly without washing the cells.

The method can be performed in semi-solid media where entirely removing unbound F-MTX is not possible. Secreted antibody and DHFR detection can be multiplexed and demonstrates that there is a correlation between expression of the two protein products. Cells which are identified as expressing DHFR (and therapeutic antibody) at a high level may be selected and picked using an automated colony picking device such as ClonePixFL.

Although the protocol refers specifically to ClonePixFL as an example of a robotic apparatus, it will be clear to the skilled reader that any robotic apparatus capable of imaging colonies and picking selected ones may be used in the method. Such a robotic apparatus will generally comprise an imager for visualising colonies and enabling selection of colonies of interest (e.g., those colonies which are labelled) and a colony picker, to enable such colonies of interest to be picked. For example, a description of a robotic apparatus is provided in the section above "Robotic Detection and Picking"; with reference to that description, the colonies may be imaged using the imaging station 100, and picked using the cell-picking head 118.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855, Lars-Inge Larsson "*Immunocytochemistry: Theory and Practice*", CRC Press inc., Baca Raton, Fla., 1988, ISBN 0-8493-6078-1, John D. Pound (ed); "*Immunochemical Protocols, vol 80*", in the series: "Methods in Molecular Biology", Humana Press, Totowa, N.J., 1998, ISBN 0-89603-493-3, Handbook of Drug Screening, edited by Ramakrishna Seethala, Prabhavathi B. Fernandes (2001, New York, N.Y., Marcel Dekker, ISBN 0-8247-0562-9); Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3; and The Merck Manual of Diagnosis and Therapy (17th Edition, Beers, M. H., and Berkow, R, Eds, ISBN: 0911910107, John Wiley & Sons). Each of these general texts is herein incorporated by reference.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments and that many modifications and additions thereto may be made within the scope of the invention. Indeed, various modifications of the described modes for carrying out the invention which are obvious to those skilled in molecular biology or related fields are intended to be within the scope of the claims. Furthermore, various combinations of the features of the following dependent claims can be made with the features of the independent claims without departing from the scope of the present invention.

What is claimed is:

1. A method of identifying a cell or cell colony which produces a polypeptide of interest, the method comprising:
   a) exposing one or more cells in a same medium to tetrahydrofolate and a marker compound comprising methotrexate which associates with a reference polypeptide comprising dihydrofolate reductase, wherein production of the polypeptide of interest by the one or more cells is linked to production of the reference polypeptide; and
   b) detecting association of the marker compound with the one or more cells, thereby identifying a cell or cell colony which produces the polypeptide of interest,
   wherein a gene encoding the reference polypeptide is amplified in the identified cell or cell colony, and wherein detecting association of the marker compound comprises (i) obtaining an image of the one or more cells and (ii) analysing the image to identify association of the marker compound with the identified cell or cell colony.

2. A method according to claim 1, wherein a gene encoding the polypeptide of interest is amplified in the identified cell or cell colony.

3. A method according to claim 1, wherein the polypeptide of interest comprises a biotherapeutic molecule.

4. A method according to claim 1, wherein the polypeptide of interest comprises an immunoglobulin or fragment thereof.

5. A method according to claim 1, wherein the polypeptide of interest comprises a receptor.

6. A method according to claim 1, wherein the polypeptide of interest comprises a recombinant polypeptide expressed by a transfected cell.

7. A method according to claim 1, wherein the polypeptide of interest and the reference polypeptide are encoded by one or more exogenous vectors introduced into the one or more cells.

8. A method according to claim 1, wherein the one or more cells are cultured cells.

9. A method according to claim 1, wherein the image is obtained and analysed by an automated imaging system.

10. A method according to claim 1, wherein the image is analysed to determine a level of the marker compound associated with the cell or cell colony, the level being indicative of an amount of the polypeptide of interest produced by the cell or cell colony.

11. A method according to claim 1, further comprising a step of exposing the one or more cells to an agent which binds to the polypeptide of interest and detecting binding of the agent to the one or more cells.

12. A method according to claim 1, wherein the one or more cells are pre-incubated with a compound comprising methotrexate.

13. A method according to claim 1, wherein the one or more cells are disposed on or in solid or semi-solid medium.

14. A method according to claim 1, wherein the polypeptide of interest is secreted by the one or more cells.

15. A method according to claim 1, wherein the reference polypeptide is an intracellular or cell surface-associated polypeptide.

16. A method according to claim 1, wherein the marker compound comprises a fluorescent label.

17. A method according to claim 16, wherein the fluorescent label comprises fluorescein, rhodamine or phycoerythrin.

18. A method of selecting a cell or cell colony which produces a polypeptide of interest from a plurality of cells, comprising detecting a cell or cell colony which produces the polypeptide of interest by a method according to any preceding claim, and selecting the cell or cell colony by picking the detected cell or cell colony.

19. A method according to claim 18, comprising:
 a) determining a level of the marker compound associated with each cell or cell colony;
 b) comparing the level to a predetermined threshold; and
 c) selecting a cell or cell colony having a level of the marker compound above the predetermined threshold.

20. A method according to claim 18, wherein a cell or cell colony which is associated with an elevated level of the marker compound is selected, thereby selecting a cell or cell colony showing an elevated amount of production of the polypeptide of interest.

21. A method according to claim 20, wherein the level of the marker compound in the selected cell or cell colony is elevated relative to a mean level of the marker compound in the one or more cells.

22. A method according to claim 18, wherein the cell or cell colony is picked by an automated cell picking device.

23. A method according to claim 1, wherein exposing the one or more cells to a marker compound is performed at least in part with the marker compound disposed in a semi-solid medium and with the one or more cells disposed in or on the semi-solid medium, and wherein obtaining an image of the one or more cells is performed while the one or more cells are still disposed in or on the semi-solid medium.

24. A method according to claim 1, wherein detecting association of the marker compound further comprises picking the cell or cell colony from a plurality of cells, and wherein the cell or cell colony picked exhibits an elevated level of association of the marker compound relative to a mean level of the marker compound in the one or more cells.

25. A method according to claim 1, wherein the one or more cells are exposed to an amount of tetrahydrofolate effective to mitigate a toxicity of the marker compound.

26. A method of identifying a cell or cell colony which produces an amplifiable marker polypeptide comprising dihydrofolate reductase, the method comprising:
 (a) exposing one or more cells in a same medium to tetrahydrofolate and a marker compound comprising methotrexate which associates with the amplifiable marker polypeptide, the amplifiable marker polypeptide comprising a product of a gene which can be amplified in the one or more cells in the presence of the marker compound; and
 (b) detecting association of the marker compound with the one or more cells, thereby identifying a cell or cell colony which produces the amplifiable marker polypeptide,
 wherein detecting association of the marker compound comprises (i) obtaining an image of the one or more cells and (ii) analyzing the image to identify association of the marker compound with the identified cell or cell colony.

* * * * *